United States Patent
Lisec et al.

(10) Patent No.: US 11,268,122 B2
(45) Date of Patent: Mar. 8, 2022

(54) METHOD OF PRODUCING A CAVITY HAVING A POROUS STRUCTURE

(71) Applicant: Fraunhofer-Gesellschaft zur Foerderung der angewandten Forschung e.V., Munich (DE)

(72) Inventors: Thomas Lisec, Itzehoe (DE); Fabian Lofink, Itzehoe (DE)

(73) Assignee: Fraunhofer-Gesellschaft zur Foerderung der anaewandten Forschunq e.V., Munich (DE)

( * ) Notice: Subject to any disclaimer, the term of this patent is extended or adjusted under 35 U.S.C. 154(b) by 533 days.

(21) Appl. No.: 15/679,885

(22) Filed: Aug. 17, 2017

(65) Prior Publication Data
US 2018/0051308 A1   Feb. 22, 2018

(30) Foreign Application Priority Data
Aug. 19, 2016   (DE) .................. 10 2016 215 617.9

(51) Int. Cl.
*C12Q 1/00* (2006.01)
*B81C 1/00* (2006.01)
(Continued)

(52) U.S. Cl.
CPC .......... *C12Q 1/002* (2013.01); *B81C 1/00182* (2013.01); *C23C 16/45525* (2013.01);
(Continued)

(58) Field of Classification Search
CPC ... H01F 1/06; H01F 41/32; H01F 3/08; H01F 2003/103; H01F 27/255; H01F 41/16;
(Continued)

(56) References Cited

U.S. PATENT DOCUMENTS 6,553,651 B2   4/2003   Reznik et al.
6,572,371 B1   6/2003   Sion et al.
(Continued)

FOREIGN PATENT DOCUMENTS

CA   2268729 A1   4/1998
CN   1171137 A   1/1998
(Continued)

OTHER PUBLICATIONS perpetuum.com, [online], Retrieved from: <http://www.perpetuum.com/products/vibration-energy-harvester.asp>.
(Continued)

*Primary Examiner* — Tabassom Tadayyon Eslami
(74) *Attorney, Agent, or Firm* — Perkins Coie LLP; Michael A. Glenn

(57) ABSTRACT

A method of producing a device includes providing a substrate which has a recess. A multitude of loose particles is introduced into the recess. A first portion of the particles is coated by using a coating process having a depth of penetration which extends from an opening of the recess, along a direction of depth, and into the recess, so that the first portion is connected to form a solidified porous structure. The depth of penetration of the coating process which extends into the recess is set such that a second portion of the particles is not connected by means of the coating, and such that the solidified first portion of the particles is arranged between the second portion of the particles and surroundings of the recess. According to the invention, the second portion of the particles is at least partly removed from the recess.

19 Claims, 10 Drawing Sheets

(51) Int. Cl.
*C23C 16/455* (2006.01)
*G01R 33/02* (2006.01)

(52) U.S. Cl.
CPC ...... *G01R 33/02* (2013.01); *B81B 2201/0235* (2013.01); *B81B 2201/054* (2013.01); *B81B 2203/0127* (2013.01); *B81B 2203/0315* (2013.01)

(58) Field of Classification Search
CPC ....... H01F 1/11; G01R 33/38; G01R 33/0052; B01J 19/0093; C23C 16/4552; C23C 16/45525; C23C 16/045; B05D 1/24; B05D 5/00; H05K 2203/308; B81B 2203/0315; C12Q 1/002; B81C 1/00182
USPC .......... 427/474, 550, 71, 174, 475; 204/557, 204/298.22
See application file for complete search history.

(56) References Cited

U.S. PATENT DOCUMENTS

| | | | |
|---|---|---|---|
| 6,573,623 B2 | 6/2003 | Tsuboi et al. | |
| 9,221,217 B2 | 12/2015 | Lisec et al. | |
| 2001/0019752 A1 | 9/2001 | Purdy et al. | |
| 2002/0197622 A1 | 12/2002 | Mcdevitt et al. | |
| 2004/0070816 A1 | 4/2004 | Kato et al. | |
| 2004/0112937 A1 | 6/2004 | Laermer | |
| 2004/0155010 A1 | 8/2004 | Benzel et al. | |
| 2004/0241034 A1 | 12/2004 | Mino et al. | |
| 2007/0134939 A1 | 6/2007 | Brueck et al. | |
| 2007/0228862 A1 | 10/2007 | Welchko et al. | |
| 2008/0024118 A1 | 1/2008 | Kahlman et al. | |
| 2008/0160787 A1 | 7/2008 | Lehmann | |
| 2009/0243780 A1 | 10/2009 | Inoue et al. | |
| 2009/0258168 A1* | 10/2009 | Barcock ............. | B22F 3/1055 427/596 |
| 2009/0280242 A1 | 11/2009 | Winarski | |
| 2009/0286402 A1 | 11/2009 | Xia et al. | |
| 2010/0123456 A1 | 5/2010 | Boeve et al. | |
| 2011/0018136 A1 | 1/2011 | Bedair et al. | |
| 2013/0058785 A1* | 3/2013 | Kellerer ............. | F01D 5/16 416/1 |
| 2013/0102121 A1 | 4/2013 | Kim et al. | |
| 2013/0169381 A1 | 7/2013 | Kim et al. | |
| 2014/0023849 A1* | 1/2014 | Lisec ............... | C23C 16/01 428/306.6 |
| 2015/0111062 A1* | 4/2015 | Shen ............... | C23C 14/5873 428/627 |
| 2015/0147217 A1 | 5/2015 | Johnson et al. | |
| 2015/0288269 A1 | 10/2015 | Ruff | |
| 2015/0361489 A1 | 12/2015 | Soper et al. | |
| 2017/0278605 A1 | 9/2017 | Lisec et al. | |
| 2018/0029002 A1 | 2/2018 | Lisec et al. | |

FOREIGN PATENT DOCUMENTS

| | | |
|---|---|---|
| CN | 1234014 A | 11/1999 |
| CN | 1650042 A | 8/2005 |
| CN | 1957257 A | 5/2007 |
| CN | 102027572 A | 4/2011 |
| CN | 104042214 A | 9/2014 |
| DE | 10118568 A1 | 10/2002 |
| DE | 102005010080 A1 | 9/2006 |
| DE | 102007051977 A1 | 9/2008 |
| DE | 102007029445 A1 | 12/2008 |
| DE | 102011000486 A1 | 8/2012 |
| DE | 102011010899 A1 | 8/2012 |
| DE | 102014226138 A1 | 6/2016 |
| DE | 102015206377 A1 | 10/2016 |
| EP | 2584588 A1 | 4/2013 |
| JP | 2005-5213556 * | 8/2005 |
| JP | 2006032466 A | 2/2006 |
| JP | 2009088502 A | 4/2009 |
| JP | 2011173749 A | 9/2011 |
| WO | 2008106928 A2 | 9/2008 |
| WO | 2016/096636 * | 6/2016 |

OTHER PUBLICATIONS

"Fensterbaufirmen—Längenmessung", Intertronic Gresser GmbH; [online] retrieved from http://www.interpatent.de/fensterbaufirmen_laengenmessung.html Mar. 15, 2018, 2010, 1-4.

"http://sensitec.com/deutsch/produkte/winkel/winkelmessung-erlaeuterung.html", Springer-VDI-Verlag; [online] retrieved from https://www.konstruktion-online.de/Heftarchiv/2017/Ausgabe-S2/Messen-Pruefen-Ueberwachen/Neuentwicklungen-bei-magnetoresistiven-Sensoren-fuer-intelligente-Lager on Mar. 1, 2017, The picture referred to has been found on a different website. 3 screenshots as one file are attached., 2017, 1-3.

"http://www.bogen-electronic.com/Lineare_Massstaebe.html", BOGEN Electronic GmbH; [online] retrieved from http://www.bogen-electronic.com/files/bilder/PDF/Technical_Data_Sheet_LMS.pdf Mar. 15, 2018, 1-7.

Achayya, A. et al., "Experimental Study on the Effect of Magnetic Field on Current-Voltage Characteristics of N-Channel Enhancement-Type MOSFET", Journal of Electron Devices, vol. 13, 2012, 945-948.

Ando, B. et al., "Nonlinear Mechanism in MEMS Devices For Energy Harvesting Applications", J. Micromech Microeng 20 125020, 2010, 1-12.

Clark, J. J. , "CMOS Magnetic Sensor Arrays", Proc. IEEE Solid-State Sensor and Actuator Workshop, 1988.

Galchev, T. et al., "Non-Resonant Bi-Stable Frequency-Increased Power Scavenger From Low-Frequency Ambient Vibration", Proc. IEEE Transducers, Jun. 21-25, 2009.

Li, X. et al., "Li Non-Resonant Electromagnetic Energy Harvester for Car-Key Applications", PowerMEMS Journal of Physics: Conference Series 476 012069, 2013.

Najafi, K. et al., "Microsystems for Energy Harvesting", Proc. IEEE Transducers, Jun. 5-9, 2011.

Oniku, Ololade D. et al., "Permanent magnet microstructures using dry-pressed magnetic powders", IOP Publishing; Journal of Micromechanics and Microengineering 23 (2013), doi 10.1088/0960-1317 /23/7/075027, Jun. 12, 2013, 1-11.

Reimer, Tim et al., "Temperature-stable NdFeB micromagnets with high-energy density compatible with CMOS back end of line technology", MRS Advances, 1:3 (Jan. 2016) pp. 209-213, DOI: 10.1557/adv.2015.19,, Dec. 25, 2015, 2019-213.

Xu, Zhi-Hao et al., "Grooved multi-pole magnetic gratings for high-resolution positioning systems", Japanese Journal of Applied Physics 54, 2015, http://dx.doi.org/10.7567/JJAP.54.06FP01, Apr. 15, 2015, 06FP01-1 to 06FP01-5.

Yang, Tzu-Shun et al., "Fabrication and characterization of parylene-bonded Nd—Fe-8 powder micromagnets", American Institute of Physics, Journal of Applied Physics 109, 07 A753 (2011), doi: 10.1063/1.3566001, Apr. 12, 2011, 07A753-1 to 07A753-3.

Zhi, Chao et al., "A polydimethylsiloxane diaphragm integrated with a sputtered thin film NdFeB magnet", Microsystem Technologies (2015) 21:675-681, DOI 10.1007/S00542-014-2085-z, Jan. 28, 2014, 675-681.

Aoyagi, I., et al., "A Raster-Output 2D MEMS Scanner With an 8x4 MM Mirror For An Automotive Time-Of-Flight Image Sensor", W3P.129978-1-4673-5983-2/13 IEEE, 2321-2324.

Egelkraut, Sven, et al., "Polymer Bonded Soft Magnetic Particles For Planar Inductive Devices", Proc. CIPS, 1-8.

Feng, Y., et al., ", All-Polymer high-aspect-ratio spring with embedded electrode", Proc. IEEE Transducers Conf., Barcelona, Spain, 2013.

Gardner, Donald S., et al., "Review of On-Chip Inductor Structures With Magnetic Films", IEEE Transactions on Magnetics, vol. 45, No. 10, Oct. 2009, 4760-4766.

Glickman, Michael, et al., "High-Performance Lateral-Actuating Magnetic MEMS Switch", Journal of Microelectromechanical Systems vol. 20, No. 4, 842-851.

(56) References Cited

OTHER PUBLICATIONS

ILIC, ", Fabrication of flexible polymer tubes for micro and nanofluidic applications", J. Vac. Sci. Technol. B 20 (6) Nov./Dec. 2002.

Jiahao, Zhao, et al., "Fabricate High Performance RF-MEMS Inductor With A Smart Nano Magnetic Granular Film According to Function Purpose", Proceedings of the 13th IEEE International Conference on NanotechnologyBeijing, China, 789-793.

Lee, Dok Won, et al., "Design and Fabrication of Integrated Solenoid Inductors with Magnetic Cores", Electronics Components and Technology ConferenceIEEE 978-1-4244-2231-9/08, 2008,701-705.

Lei, et al., ", Molecular Effusion-Boltzmann model for parylene C deposition in deep trench", Proc. IEEE Nano/Micro Engineered and Molecular Systems Conf., Xiamen, China, 2010.

Leidich, Stefan, et al., "HF-MEMS Schalter Mit Ohmschen Kontakt Und Lateraler Bewegungsrichtung RF-MEMS Switch With Ohmic Contact and Lateral Actuation", Mikrosystemtechnik Kongress Poster 12.1, 976-979.

Lyshevski, Sergey E., et al., "Ferrite Nanoparticles for MEMS Technology Sensors and Actuators", 11th IEEE International Conference on NanotechnologyPortland Marriott, Aug. 2011, 1252-1256.

Mano, Yasuhiko, et al., "Planar Inductor With Ferrite Layers For DC-DC Converter", Transducers'05 The13th International Conference on Solid-State Sensors, Actuators and Microsystems, 891-894.

Oniku, Ololade D., et al., ", Permanent magnet microstructures using dry-pressed magnetic powders", J. Micromech. Microeng. 23 (2013).

Raj, P. Markondeya, et al., "Novel Nanomagnetic Materials For High-Frequency RF Applications", Electronics Components and Technology Conference, 2011, 1244-1249.

Rassel, Richard J., et al., "Fabrication and Characterization of a Solenoid-Type Microtransformer", IEE Transactions of Magnetics vol. 39, No. 1, Jan. 2003, 553-558.

Robbins, R., "", Cleanroom Research Laboratory, htttps://research.utdallas.edu/cleanroom/manuals/scs-parylene-deposition; Dec. 10, 2010 (update Jan. 15, 2014), Dec. 10, 2010.

Sawant, Shashank G., et al., "Fabrication, Characterization, and Modeling of Fully-Batch_Fabricated Piston-Type Electrodynamic Microactuators", Journal of Microelectromechanical Systems, vol. 23, No. 1, Feb. 2014, 220-229.

Sun, Xu-Ming, et al., "Electrodeposition and Characterization of CoNiMnP-based Permanent Magnetic Film For MEMS Application", Proceedings of the 2011 6th IEEE International Conference on Nano/Micro Engineered and Molecular SystemsKaohsiung, Taiwan, 367-371.

Yang, C., et al., "On-Chip RF Inductors With Magnetic Nano Particles Medium", Th1B.005 Transducers 11, 2801 -2804.

Yang, Tzu-Shun, et al., ", Fabrication and characterization of parylene-bonded Nd—Fe—B powder micromagnets", J. Appl. Phys., vol. 109, 07A753 (2011).

Yang, Tzu-Shun, et al., "Fabrication and Characterization of Parylene-Bonded Nd—Fe—B Powder Micromagnets", Journal of Applied physics 109, 07A753 American Institute of Physics, 1-4.

Yu, Xuehong, et al., "Silicon-Embedded Toroidal Inductors with Magnetic Cores: Design Methodology and Experimental Validation", Proc. APECFort Worth, TX, 763-767.

Zhan, Jing , et al., "Stacked-Spiral RF Inductor With Vertical Nano-Powder Magnetic Core in CMOS", Iee Microwave and Wireless Components Letters, vol. 22, No. 1,29-31.

* cited by examiner

METHOD OF PRODUCING A CAVITY HAVING A POROUS STRUCTURE

CROSS-REFERENCE TO RELATED APPLICATIONS

This application claims priority from German Patent Application No. 10 2016 215 617.9, which was filed on Aug. 19, 2016, and is incorporated herein in its entirety by reference.

The invention relates to a method of producing a cavity having a porous structure, and to a device having a porous structure and a cavity.

BACKGROUND OF THE INVENTION

Manufacturing of porous ceramics or metals per se has been industrially established. Many methods have been known, which range from sintering of powders to pyrolysing of ceramic/polymer foams. All of said methods have in common that temperatures of clearly above 400° C. may be used in most cases. In addition, blanks of the porous material are created which first of all need to be brought into the form that may be used for a specific application and then have to be integrated, by means of further processing steps, into a cavity that may be used.

An advantageous method of producing porous structures is described in DE 10 2011 010 899 A1. In said document, loose particles are integrated into or applied onto a carrier element. A coating solidifies the loose particles to form a contiguous porous structure. A specific embodiment of DE 10 2011 010 899 A1 describes producing of a cavity by means of two halves of a substrate while removing the entire porous structure. A lower half of the substrate is filled with loose particles, which are completely solidified to form a composite structure. A further material, which will form a membrane later on, may be applied onto the composite structure. An upper half of the substrate is placed onto the lower half of the substrate, and subsequently, the composite structure is completely removed, so that only the membrane consisting of the other kind of material remains. Alternatively, the membrane consisting of the other material may also be omitted, so that following complete removal of the composite structure, a completely empty cavity is formed between the two halves of the substrate.

Manufacturing of such cavities involves many individual process steps, and its implementation therefore involves a large amount of expenditure. Such a method can therefore be implemented only with a large amount of expenditure in terms of time and cost.

SUMMARY

According to an embodiment, a method of producing a device may have the steps of: providing a substrate having a recess; introducing a multitude of loose particles into the recess; coating a first portion of the particles, so that the first portion is connected to form a solidified porous structure, while using a coating process having a depth of penetration which extends from an opening of the recess, along a direction of depth, and into the recess; wherein the depth of penetration of the coating process into the recess is set such that a second portion of the particles is not connected by means of the coating, so that the solidified first portion of the particles is arranged between the second portion of the particles and surroundings; and selectively removing from the recess, at least partly, the second portion of the particles which is enclosed and has remained uncoated, while maintaining the porous structure, a cavity forming between the recess provided within the substrate and that portion of the particles which has solidified to form the porous structure.

According to another embodiment, a device may have: a substrate having a recess, and a porous structure which is arranged within or at the recess such that a cavity remains between the recess provided within the substrate and the porous structure, wherein the porous structure has a multitude of particles which are connected to one another by means of a coating and are solidified to form the porous structure, and wherein less than 90% of the volume of the cavity is filled with loose particles.

In accordance with the inventive method, a substrate comprising a recess is initially provided. A plurality of loose particles is introduced into the recess. By using a coating process, a first portion of the particles is coated, specifically in such a manner that the first portion is connected to form a solidified porous structure. For this purpose, the coating process has a depth of penetration which extends from an opening of the recess, along a direction of depth, and into the recess. In other words, the coating penetrates the particles from the top in the direction of the recess. The depth of penetration of the coating process into the recess is set such that a second portion of the particles is not connected by means of the coating. This means that only a part, or a portion, of the particles located within the recess is solidified by means of the coating, advantageously that part of the particles which lies on top. The first portion of the particles, which is solidified to form the porous structure, is thus arranged between the second portion of the non-solidified, loose particles and surroundings of the recess. In other words, the non-solidified second portion of the particles, i.e. the non-solidified loose particles, is enclosed within a cavity which is formed between the recess and the first portion of the particles, which is solidified to form the porous structure. Thus, the cavity is formed between the recess provided within the substrate and the porous structure. The porous structure provides a lid, as it were, of the otherwise open recess. The cavity is not completely filled with the non-solidified second portion of the particles at this point in time. According to the invention, this second portion of the particles, i.e. the non-solidified loose particles located below the porous structure, is at least partly removed from the recess. Partial removal of the second portion of the particles shall be understood to mean that a specific portion of the original number of the second portion of the particles is removed from the recess. As was mentioned at the outset, the second portion of the particles is enclosed within the cavity formed between the recess and the porous structure. The non-solidified loose particles, i.e. the second portion of the particles, are densely packed. In other words, the loose particles are distributed across the entire cavity and fill up the entire volume of the cavity. At least some of said loose particles are now removed, so that larger free spaces are formed between the individual particles as compared to the original filling quantity. Accordingly, the remaining loose particles fill up less volume within the cavity. Thus, once some of the non-solidified loose particles (second portion of the particles) have been removed, there will be fewer particles within the cavity than were originally introduced into the recess. At the same time, however, the first portion of the particles, i.e. the particles solidified to form the porous structure, remains. Thus, only the non-solidified loose particles enclosed within the cavity are selectively removed, whereas the porous structure is maintained. The coating resulting in the solidification of the loose particles and, therefore, in the formation of the porous structure may furthermore couple the porous structure to the substrate and/or to the recess of the substrate, so that the porous structure is connected to the substrate and/or fixated on the substrate. A medium such as air or water, for example, which surrounds the substrate may diffuse into the recess through the porous structure.

It is conceivable for at least 10% or at least 25% of the second portion of the particles to be removed from the recess. Thus, loosening of the previously densely packed loose particles may occur. Therefore, a cavity is provided which is at least partly filled with loose particles, the cavity comprising a porous structure through which, e.g., liquids or gases may diffuse so as to enable fluidic communication of the cavity with the surroundings.

In accordance with a further feasible embodiment, more than 50% of the second portion of particles may be removed from the recess. I.e., less than half of the cavity is now filled with loose particles. The loose particles remaining within the cavity thus have a lot of free space for moving inside the cavity.

It is feasible for the second portion of the particles to be removed essentially completely. I.e., the non-solidified loose particles enclosed within the cavity are removed completely from the cavity. Thus, a cavity may be provided which is essentially free from particles.

The second portion of the particles, i.e. the non-solidified loose particles, may be removed by means of an etching process. To this end, common wet- or dry-chemical etching processes may be used, for example. The respective etchant may diffuse into the recess through the porous structure, for example, so as to etch off the underlying loose particles. However, it is also feasible for the etchant to be introduced into the recess through an opening provided within the substrate.

It is conceivable for the first portion of the particles to comprise a material different from that of the second portion of the particles. I.e., the solidified porous structure comprises particles consisting of a material (e.g. material C) different from that of the non-solidified loose particles enclosed within the cavity (e.g. material A and/or material B). This is advantageous in that an etchant suitable to remove the non-solidified loose particles will not attack the porous structure.

In accordance with an embodiment, loose particles comprising a first material may be introduced into the recess first, and subsequently, loose particles comprising a second material may be introduced into the recess, the particles comprising the second material being coated subsequently. I.e., loose particles consisting of a material A may first be introduced into the recess, for example. Subsequently, loose particles consisting of a material B are applied onto the loose particles consisting of material A. The loose particles consisting of material B thus lie on top of the loose particles consisting of material A. The coating may be such that it solidifies only those particles to form a porous structure which lie on top and consist of material B. The underlying loose particles consisting of material A, however, are not solidified by the coating since the coating either does not reach them or since the material A does not react with the coating to form a porous structure. Thus, selective solidification of loose particles may be provided. Moreover, the cavity may have an etchant introduced therein which dissolves only the non-solidified loose particles consisting of material A, whereas the porous structure consisting of the solidified particles of material B is not attacked by the etchant.

It is further conceivable for a coating, in particular a passivation layer, to be applied onto the porous structure, so that the coating extends, at least in portions, across the substrate and/or, at least in portions, across the porous structure. For example, a passivation layer may be applied which covers the substrate and a portion of the porous structure which is arranged close to the substrate,. The center, or an internal part of the porous structure, may be left open, so that gases, liquids, etc. may continue to diffuse through the left-open part of the porous structure. In other words, an opening through which the porous structure remains in contact with its surroundings is left open in the passivation layer.

However, the coating may also be applied onto the porous structure such that it fully covers the porous structure and seals the porous structure in a fluid-tight manner. Fluid-tight sealing may be advantageous in terms of protecting the cavity, or the recess, from penetration of humidity and/or dirt.

It is feasible that at least one inner side of the recess has, at least in portions, a layer applied onto it which reduces the adhesive forces and/or frictional forces between the recess and a particle and/or object which remains within the recess once the second portion of the particles has been at least partly removed, and/or has a layer applied onto it which reduces the radiation emanating from a particle and/or object which remains within the recess once the second portion of the particles has been at least partly removed. The recess provided within the substrate comprises, as is common, a lower side, or bottom, and circumferential side walls which overall may also be referred to as inner walls. The coating may be applied, e.g., only onto the lower side or only onto one of the side walls. However, the coating may also be applied onto all inner sides of the recess. For example, the coating may serve to reduce, or avoid, adhesion of particles and/or objects which are located within the cavity, i.e. the coating may be a non-stick coating, for example. However, the coating may also perform a function of reducing and/or shielding off radiation. For example, the coating may be a metal coating.

It is conceivable for the multitude of loose particles to comprise particles having a magnetic material. This means, the multitude of loose particles may include one of more particles comprising or consisting of a magnetic material. For example, one or more magnetic particles may be present within the cavity as non-solidified loose particles in addition to the multitude of non-solidified loose particles present within the cavity. In the process step of removing the loose particles, it is possible, for example, to remove only the non-magnetic loose particles, so that only the magnetic loose particles remain within the cavity. Thus, a cavity having magnetic particles enclosed therein is provided in a simple manner, said cavity additionally being covered by a porous structure.

It is feasible that for producing the porous structure, the coating process by means of which the first portion of the particles is coated is an ALD (atomic layer deposition) process. Said process is self-limiting, so that very good process management with regard to forming the layer thickness of the coating process is possible. I.e., the thickness of the porous structure may be determined in a highly accurate manner by means of an ALD process.

In accordance with an embodiment of the inventive method, at least one object may be introduced into the recess, in addition to the multitude of loose particles, prior to coating of the first portion of the particles. For example, the multitude of loose particles may be filled into the recess at the same time as said at least one object, i.e. in the form of a mixture. It is also feasible, however, to first of all introduce a layer of loose particles into the recess and to subsequently introduce said at least one object, and to subsequently introduce a further layer of loose particles, so that said at least one object is enclosed by two or more layers of loose particles. Said at least one object and the loose particles are introduced into the recess either at the same time or in succession, as it were.

It is conceivable for the at least one object to be a particle comprising a material different from that of the multitude of loose particles, or for the at least one object to be a molded body comprising a material different from that of the multitude of loose particles. Therefore, if the at least one object is a particle, it would therefore be feasible for a mixture of particles, which comprises individual particles comprising a material A and individual particles comprising a material B, to be present within the recess. That portion of the mixture of particles which is not solidified following the coating process would therefore correspond to the second portion of loose particles. As was described above, the step of at least partly removing the second portion of the loose particles may be performed selectively. I.e., selective removal of individual particles from the mixture of particles may take place, for example, specifically such that only individual particles having a specific material (e.g. only individual particles comprising material A) are removed from the mixture of particles, whereas individual particles comprising the respectively other material (e.g. individual particles having material B) remain within the recess. If the at least one object is a molded body it would be feasible for the molded body to be present within the recess together with the multitude of loose particles. Once the second portion of particles has been at least partly removed, the molded body remains within the cavity in addition to any particles which may not have been removed. If the particles have been completely removed, the molded body will remain within the cavity by itself. The molded body enclosed within the cavity may freely move therein, for example, provided that it is smaller than said cavity.

The at least one object may have a magnetic property, for example. I.e., the object (particle or molded body) may comprise or consist of a magnetic material. The object may be a magnetic molded body, for example, which remains within the cavity by itself once the non-solidified loose particles have been removed. Thus, one will obtain a magnet enclosed within the cavity, as it were, which may freely move inside the cavity, for example. This may be exploited, e.g., for detecting changes in location.

In accordance with an embodiment of the inventive method, the at least one object may be introduced into the recess in a demagnetized state and may be magnetized prior to or following at least partial removal of the second portion of the particles. This is useful, e.g., if magnetic properties of the object prior to removal of the non-solidified loose particles are undesired or if subsequently, processes need to be performed at temperatures which would exert too much influence on the magnetic properties.

It is also feasible for a magnetic field sensor system to be arranged at the substrate so as to determine the magnetic field of the at least one object by means of the magnetic field sensor system. For example, one may use known magnetic field sensors which are formed "on-chip" within the substrate. Thus, such a magnetic field sensor is arranged directly at the substrate. However, it is also feasible for a magnetic field sensor to be arranged at a separate carrier and for the carrier in turn to be connected to the substrate. Therefore, such a magnetic field sensor is indirectly arranged at the substrate, i.e. by means of the separate carrier.

In accordance with further feasible implementations of the inventive method, a coil interacting with the at least one object may be arranged at the substrate so as to generate, by means of a relative movement between the coil and the at least one object, an induced voltage which forms within the coil, or to exert a magnetic induction force on the at least one object by means of an electric current flowing through the coil. The coil may be integrated into the substrate, for example. Such a coil is therefore arranged directly at the substrate. However, it is also feasible for an external coil, or an external coil array, to be arranged at the substrate. Such a coil is therefore indirectly arranged at the substrate, i.e. by means of a separate carrier. It is also feasible for the coil to be arranged at the further layer, in particular the passivation layer. In this case, too, the coil would be indirectly arranged at the substrate, i.e. via the passivation layer.

It is conceivable for an opening to be introduced into the substrate in that side of the substrate which is opposite the porous structure, said opening providing a fluid connection between the recess or the cavity and the surroundings. Thus, e.g., a fluid inlet and/or a fluid outlet may be provided. This is advantageous in particular for producing systems through which a fluid flows, e.g. for measuring flows of fluid. For example, the porous structure may serve as a fluid inlet, and the opening may serve as a fluid outlet, or vice versa.

In this context it is conceivable for the cross section of the opening to be smaller than an object which remains within the recess once the second portion of the particles has been at least partly removed, so that the opening may be closed by means of the object so as to suppress the fluid connection to the surroundings. The object, e.g. a molded body, may act as a lid and/or valve disk closing the opening. The object may close the opening and unblock the opening as needed.

Generally, provision of the substrate may include provision of a substrate having a circular recess and/or an elongated recess. The recess provided within the substrate may therefore be, e.g., an elongated (e.g. milled or etched) trench, a bore or a blind hole. The recess may also be configured in the form of a donut and/or a toroid (annular trench).

The invention further relates to a device comprising a substrate having a recess, and a porous structure arranged within or at the recess such that a cavity remains between the recess and the porous structure. I.e., the bottom and the side walls of the recess which surround the bottom form the cavity together with the porous structure. The porous structure is arranged opposite the bottom of the recess. For example, the porous structure may be arranged above the opening of the recess, i.e. on the substrate, or be arranged at a small distance into the recess. The porous structure comprises a multitude of particles which are interconnected by means of a coating and are solidified to form the porous structure. This distinguishes the inventive porous structures from other conventional porous structures, which can be seen, e.g., in a sectional image under the microscope. Less than 90% of the volume of the cavity formed by the recess and by the porous structure is filled with loose particles. The porous structure is a self-supporting structure which is not supported on the loose particles. The self-supporting porous structure may be a self-supporting porous membrane, for example. The invention thus provides a device comprising a cavity having a self-supporting porous structure and/or a cavity covered by means of a self-supporting porous structure. The cavity may be filled with particles up to 90% of its volume or less; at least some of said particles may comprise a material which is the same as that of the particles contained within the porous structure. Due to the fact that not the entire cavity is fully filled up with particles, the particles may move relatively freely inside the cavity. Thus, a cavity is provided which is not completely filled up with loose particles while having a porous structure so as to thereby enable fluidic communication of the cavity with its surroundings. The particles may also be present in the form of a mixture of particles which consists of particles having different materials.

In accordance with an embodiment, less than 75% or less than 50% or less than 10% of the volume of the cavity may be filled with the loose particles. Also, it would be feasible for the cavity to comprise none of said loose particles. Thus, a device would be provided here which has a cavity which is essentially free from the above-mentioned particles.

It is feasible for the loose particles present within the cavity to have a material different from that of the particles solidified to form the porous structure. This would be advantageous, for example, if the loose particles present within the cavity are removed by means of an etchant. In this case, it would be useful for the loose particles to comprise a material which may be attacked by the etchant, and for the particles solidified to form the porous structure to comprise a material which is not attacked by the etchant so as to maintain the porous structure.

In accordance with an embodiment, the cavity may have at least one object arranged therein, said at least one object being a particle comprising a material different from that of the loose particles present within the cavity, said at least one object being a molded body comprising a material different from that of the loose particles present within the cavity. Thus, if some of the above-mentioned loose particles are still present within the cavity, the at least one object may be provided within the cavity in addition to said loose particles. However, it would also be feasible that upon complete removal of all of said loose particles, only said at least one object (or even several such objects) comprising a material different from that of the loose particles is present inside the cavity. The at least one object may be a particle or a molded body. It would also be feasible for one or more particles which consist(s) of a different material (as compared to the above-mentioned loose particles), and/or for a molded body consisting of a different material to be enclosed within the cavity. A molded body is advantageously a three-dimensional molded body. It may be a molded body composed of several particles or a molded body manufactured in accordance with conventional methods, i.e. injection molding, sintering and the like.

It is conceivable for the at least one object to exhibit a magnetic property. The at least one object may exhibit, e.g., a hard magnetic or a soft magnetic property. The at least one object may be any magnet. The at least one magnetic object may be smaller than the volume of the recess, so that the magnetic object may freely move inside the recess. This offers the advantage that the at least one object moves inside the recess upon, e.g., a change in location, upon a change in position or upon acceleration of the device. By means of a suitable sensor system, said movement of the magnetic object within the recess may be determined.

Accordingly, it is advantageous for a magnetic field sensor system to be arranged at the substrate, said magnetic field sensor system being configured to determine the magnetic field of the at least one object. The magnetic field sensor system may be integrated into the substrate, for example. Such a magnetic field sensor system is thus directly arranged at the substrate. However, it is also feasible for an external magnetic field sensor system to be arranged at the substrate. Such an external magnetic field sensor system is thus indirectly arranged at the substrate, e.g. by means of a separate carrier. It is also feasible for the magnetic field sensor system to be arranged at the further layer, in particular passivation layer. In this case, too, the magnetic field sensor system would be indirectly arranged at the substrate, i.e. via the passivation layer.

Also, it would be feasible for a coil to be arranged at the substrate which interacts with the at least one object and is configured to generate, by means of a relative movement between the coil and the at least one object, an induced voltage which forms within the coil, or to exert a magnetic induction force on the at least one object by means of an electric current flowing through the coil. The coil may be integrated into the substrate, for example. Such a coil is therefore arranged directly at the substrate. However, it is also feasible for an external coil, or an external coil array, to be arranged at the substrate. Such a coil is therefore indirectly arranged at the substrate, i.e. via a separate carrier. It is also feasible for the coil to be arranged at the further layer, in particular the passivation layer. In this case, too, the coil would be indirectly arranged at the substrate, i.e. via the passivation layer.

It is conceivable that the porous structure comprises a multitude of particles having magnetic properties. Thus, the porous structure would exhibit a magnetic property. For example, if one or more objects are present within the cavity which also exhibit magnetic properties, said one or more objects might interact with the magnetic porous structure. For example, the porous structure might thus be magnetized (e.g. by means of a coil) such that it attracts and retains the magnetic object. Thus, e.g. a magnetic-valve functionality might be provided by means of the inventive device.

It is feasible for a coating, in particular a passivation layer, to be applied onto the porous structure, so that the coating extends, at least in portions, across the substrate and/or extends, at least in portions, across the porous structure. Such an additional layer might serve, e.g., to seal off the porous structure so as to protect it against penetration of, e.g., dirt, dust, humidity and the like. For example, it is also possible for the additional layer to extend only partly across the porous structure, so that part of the porous structure still is exposed to its surroundings.

It would be conceivable for the coating to fully cover the porous structure and to seal off the porous structure in a fluid-tight manner. Such a coating may be effected, e.g., by means of an epoxy matrix, by means of silicone or by means of a rubber material.

In accordance with an embodiment, that side of the substrate which is located opposite the porous structure may have an opening in the substrate formed therein which provides a fluid connection between the recess and its surroundings. Said opening may therefore serve to provide a fluid inlet and/or a fluid outlet, so that the recess may fluidically communicate with its surroundings.

In this context it is feasible for the cross section of the opening to be smaller than an object present inside the cavity, so that the opening may be closed by means of the object so as to suppress fluid communication with the surroundings. Also, a valve functionality may be provided by means of the object, in which case the object may selectively unblock and/or close the opening.

The substrate may comprise a circular recess and/or an elongated recess. The recess provided within the substrate may therefore be, e.g., an elongated (e.g. milled or etched)

trench, a bore or a blind hole. The recess may also be configured in the form of a donut and/or a toroid (annular trench).

BRIEF DESCRIPTION OF THE DRAWINGS

Embodiments of the present invention will be detailed subsequently referring to the appended drawings, in which.

DETAILED DESCRIPTION OF THE INVENTION

Figure 1A:
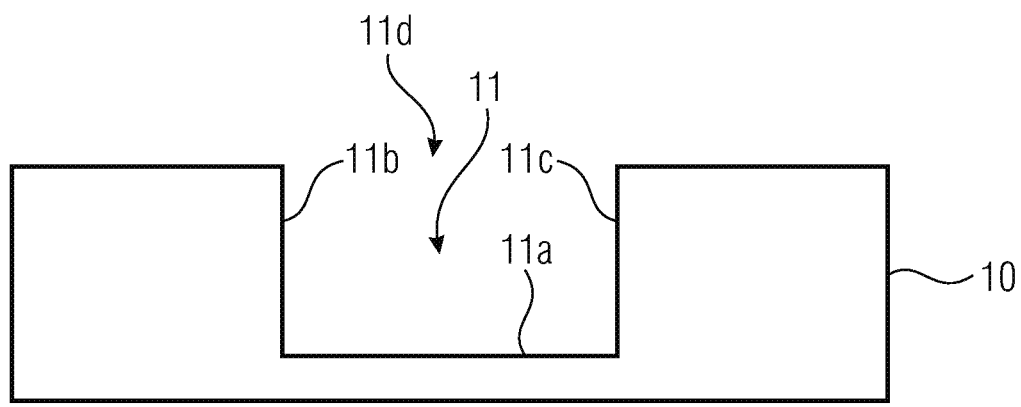
FIGS. 1a to 1d show a schematic representation of the inventive method.

Before embodiments of the present invention will be explained in more detail below with reference to the drawing, it shall be noted that elements, objects and/or structures which occur in the various figures and are identical and/or have identical functions and/or actions will be referred to by identical reference numerals, so that the descriptions of said elements which are provided in different embodiments are interchangeable and/or mutually applicable.

FIGS. 1a to 1d show an embodiment of an inventive method. In FIG. 1a, a substrate 10 is initially provided. The substrate 10 comprises a recess 11. The recess 11 comprises a bottom 11a, lateral walls 11b, 11c, and an opening 11d facing the surroundings.

Figure 1B:
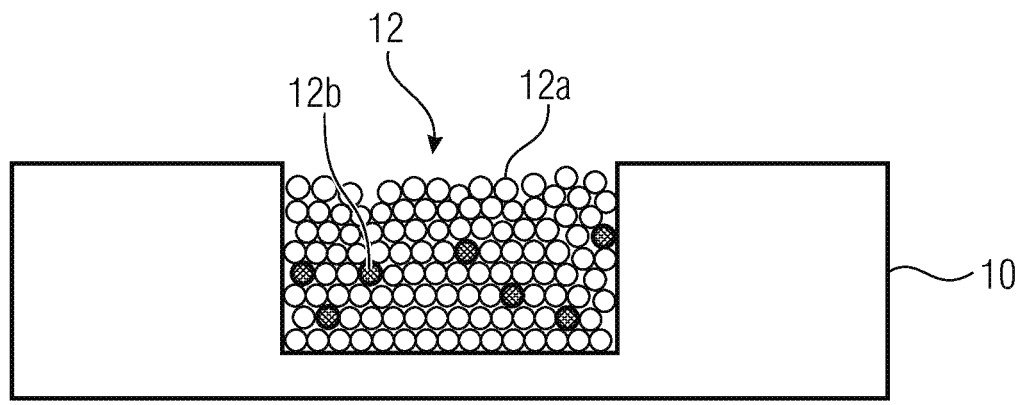

FIG. 1b shows that a multitude of loose particles 12 are introduced into the recess 11. This may be effected, e.g., by pouring particles 12, which are present as loose bulk material, into the recess 11, or by using a doctor blade on them, and the like. The multitude of loose particles 12 may consist merely of particles of the same type. However, the multitude of loose particles may also comprise different particles.

Figure 1C:
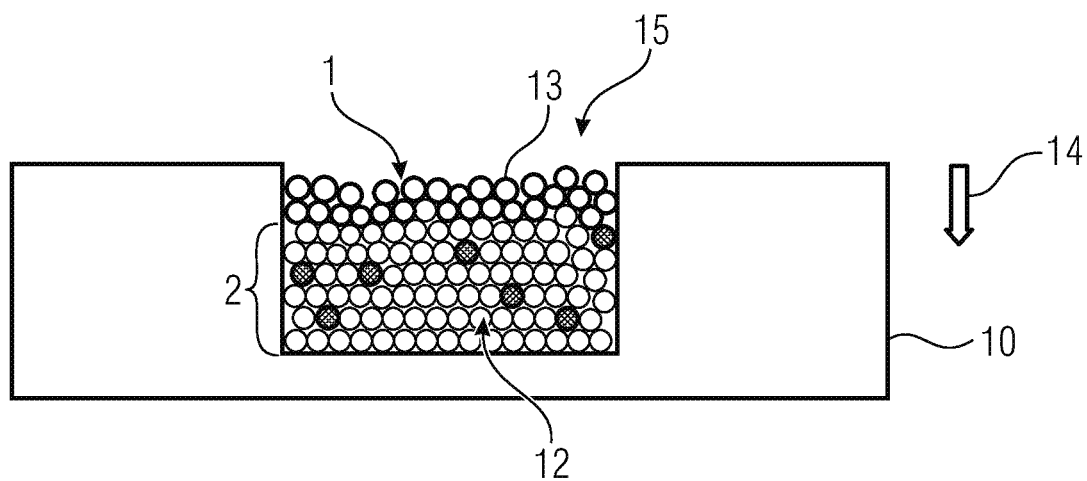

For example, the multitude of loose particles 12 depicted in FIGS. 1b and 1c comprise a first type of loose particles 12a and a second type of loose particles 12b. The number of different particles may be the same. As is shown in the figures, however, the number of the first type of loose particles 12a may clearly exceed the number of the second type of loose particles 12b, e.g. by a factor of 20 or more.

A first portion 1 of the loose particles 12 is coated while using a coating process. The coating process results in that the loose particles 12 enter into a connection with said coating and are solidified to form a porous structure 13. The coating process may be controlled such that by means of suitable process management, a depth of penetration of the coating which extends from the opening 11d of the recess 11, along a direction of depth 14, and into the recess 11 may be determined. I.e., the thickness (in the direction of depth 14) of the forming porous structure 13 may be defined, or determined.

In accordance with the invention, the depth of penetration of the coating process into the recess 11 is set such that a second portion 2 of the particles 12 is not connected by means of the coating. I.e., the second portion 2 of the loose particles 12 does not solidify to form a porous structure, but the second portion 2 of the loose particles 12 continues to exist in the form of loose particles.

In accordance with the invention, the second portion 2 of the loose particles 12 is arranged between the first portion 1 of the loose particles 12, which has been solidified to form the porous structure 13, and the interior (bottom 11a, side walls 11b, 11c) of the recess 11. In other words, the second portion 2 of loose particles 12 is arranged within a cavity forming between the recess 11 and the porous structure 13. Differently speaking, the first portion 1 of the particles 12, which has solidified to form the porous structure 13, is arranged between the second portion 2 of the particles 12 and surroundings 15 of the recess 11. Surroundings 15 are understood to mean the environment within which the substrate 10 is located, i.e. the medium surrounding the substrate 10.

As can be seen in FIG. 1c, that part of the particles 12 introduced into the recess 11 which lies on top is coated, so that the coated particles 12 solidify to form the porous structure 13. As a result, the underlying, non-coated particles 2, which thus remain loose, directly adjoin the lower side of the porous structure 13 once the porous structure 13 has been formed. The volume of the cavity 16 forming between the porous structure 13 and the interior 11a, 11b, 11c of the recess 11 is thus almost completely, i.e. up to 100% of its volume, filled with loose particles 12.

Figure 1D:
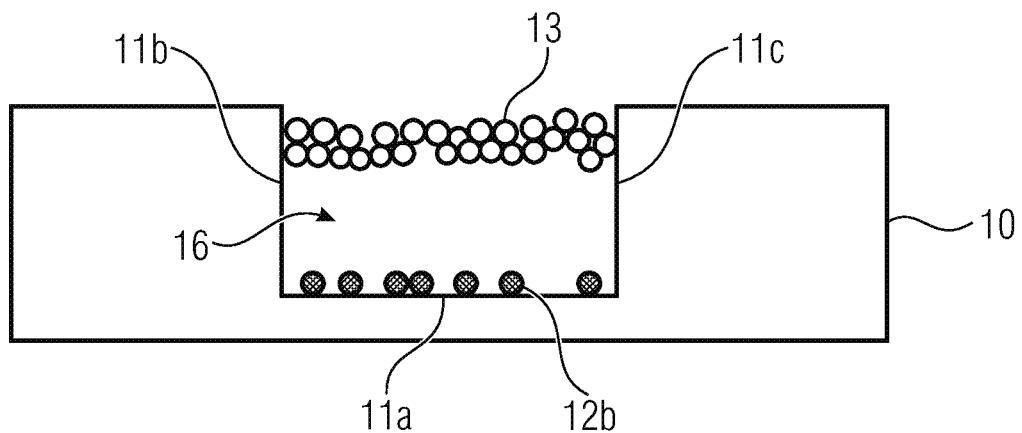

FIG. 1d shows the final product of a further step of the inventive method. Part of the second portion 2 of the particles 12 has been removed from the recess 11 between FIGS. 1c and 1d. In the present embodiment, e.g., all of the particles 12a of the first type have been removed, whereas all particles 12b of the second type have been maintained. It might just as well be feasible for all particles 12b of the second type to be removed, whereas all particles 12a of the first type are maintained. The particles 12 may, but need not, be removed completely. In accordance with the invention, the second portion 2 of the particles 12 is at least partially removed, i.e. at least 10% of the second portion of the particles 12 are removed from the recess 11.

Thus, one can see in the example shown in FIG. 1d that by removing all of the particles of the first type 12a, only the particles of the second type 12b will remain within the cavity 16. The cavity 16 forms between the bottom 11a and the sidewalls 11b, 11c of the recess 11 and the porous structure 13. The particles of the second type 12b, which remain following removal of the particles of the first type 12a, are enclosed, as it were, within the cavity 16.

In the coating process for producing the porous structure 13 it may be advantageous for the coating to be applied onto the upper side (that side which is opposite the bottom 11a of the recess 11) of the loose particles 12. Thus, the coating is applied onto the loose particles 12 which lie on top. The coating process may be an ALD (atomic layer deposition) process. Said coating process is self-limiting, i.e. the ALD coating process results in a predefined layer thickness, which will not be exceeded.

The loose particles 12, more specifically those loose particles 12 which come into contact with the ALD coating, solidify and form a solidified, but porous structure 13. The porous structure 13 is permeable to specific media such as air, for example. Accordingly, the permeable media may diffuse through the porous structure 13, i.e. either into the recess 11 or out of the recess 11.

The particles 12 which have solidified to form the porous structure 13 are also referred to as a first portion 1 of particles 12. The particles 12 present within the cavity 16 are also referred to as a second portion 2 of particles 12.

Some of the second portion 2 of particles 12 are removed in accordance with the invention. The second portion 2 of particles 12 may also be removed completely, however (not depicted). Therefore, a cavity 16 would remain which would be completely free from particles 12.

As was mentioned at the outset with reference to FIG. 1c, the second portion 2 of particles 12 may comprise a first type 12a and a second type 12b of particles 12. The second portion 2 of particles 12 is therefore a mixture of particles 12 which comprises particles of a first type 12a and particles of a second type 12b.

By means of the inventive method, some, e.g. 10% or more, of the first type 12a of particles may be removed from the mixture of particles 12 originally introduced into the recess 11. Thus, both particles of the second type 12b and the non-removed part of particles of the first type 12a are maintained within the cavity 16. However, the first type 12a of particles may also be removed completely from the mixture of particles 12, however, so that only particles of the second type 12b are maintained within the cavity 16, as is shown in FIG. 1d.

Said part of the second portion 2 of particles 12 may be removed by means of different methods. For example, an etching process may be employed for removing particles from the mixture of particles 12. By means of a suitable etchant, a specific type of particles may be etched off, or removed from, the mixture of particles 12, for example.

For example, if the mixture of particles 12 consists of silicon and silicon oxide, the silicon particles 12a in the $XeF_2$ gas phase and/or the silicon oxide particles 12b in the HF gas phase may be etched selectively with respect to the respectively other and many further materials. There are also many other possibilities of combination. Generally, dry-chemical etching processes are advantageous while wet-chemical etching process are not ruled out.

Generally, the first portion 1 of the particles 12 may have a material different from that of the second portion 2 of the particles 12. This may be achieved, e.g., in that loose particles 12 comprising a first material are introduced into the recess 11 first. Subsequently, loose particles 12 comprising a second material are introduced into the recess 11. I.e., the loose particles 12 comprising the second material are poured onto the loose particles 12 comprising the first material. Subsequently, the loose particles 12 lying on top are coated by means of the inventive coating process.

In this context it is advantageous for only the material of the loose particles 12 which lie on top to be reactive to the coating. In this manner, one achieves by using the coating process that only those loose particles 12 which lie on top will harden to form a porous structure 13. The underlying loose particles 12 consisting of the other material, however, will not harden even if they come into contact with the coating since the material of said underlying loose particles 12 is not reactive to the coating.

In other words, it may be advantageous for the solidified upper area of FIG. 1c to consist of particles 12 of a specific material C and of the solidification layer 13. This may be achieved by sequentially introducing the particles 12. Initially, the recess 11 is pre-filled with the mixture of particles 12, which includes particles 12a comprising material A as well as particles 12b comprising material B. Subsequently, the recess 11 is filled up with particles of type C in a second filling step. Subsequent solidification in the upper area is performed, with regard to the depth, such that the process is limited mainly to the particles of type C.

Figure 1E:
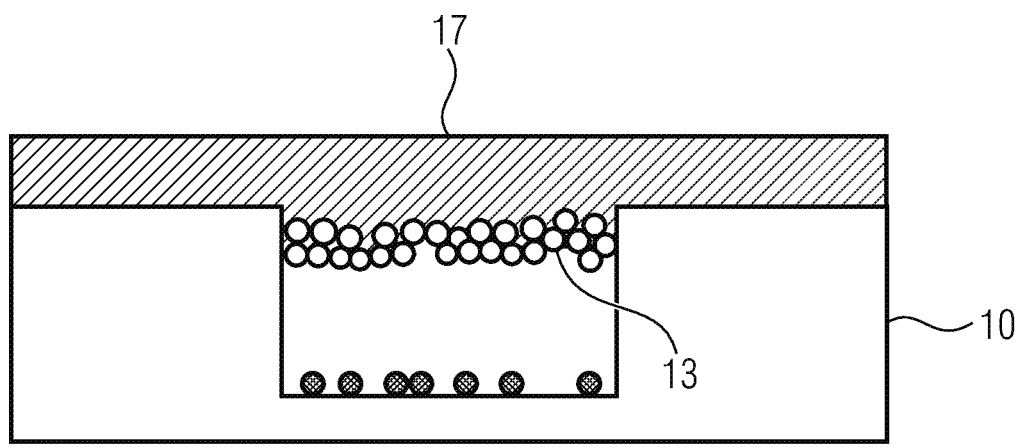
FIG. 1e shows a schematic representation of an optional step of the inventive method.

FIG. 1e shows an optional method step of the inventive method. Here, a coating 17 is applied onto the porous structure 13. The coating 17 is advantageously a passivation layer. In the embodiment shown in FIG. 1e, the coating 17 extends across the entire porous structure 13. In the embodiment shown in FIG. 1e, the coating 17 moreover extends across the entire substrate 10. The coating 17 may seal the porous structure 13 in a fluid-tight manner.

As will be described below with reference to FIGS. 7a and 7c, the coating 17 may cover the porous structure 13 and/or the substrate 10 only partly, or only in portions. By applying the coating 17 onto the porous structure 13, the cavity 16 comprising the particles 12b may be closed. If need be, the cavity 16 may be closed under vacuum or in a specific atmosphere.

As was mentioned at the outset, the multitude of particles 12 may be a mixture of particles which includes particles 12a of a first type (and of a first material) and particles 12b of a second type (and of a second material). In addition or alternatively to the particles 12b of the second type, a molded body 21, 22 may be introduced into the recess 11.

Figure 2A:
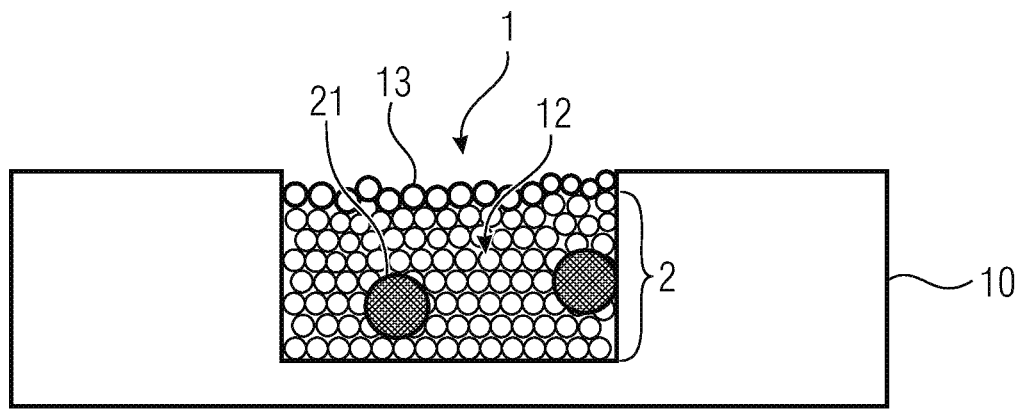
FIGS. 2a and 2b show a schematic representation with molded bodies present in the multitude of loose particles.
Figure 2B:
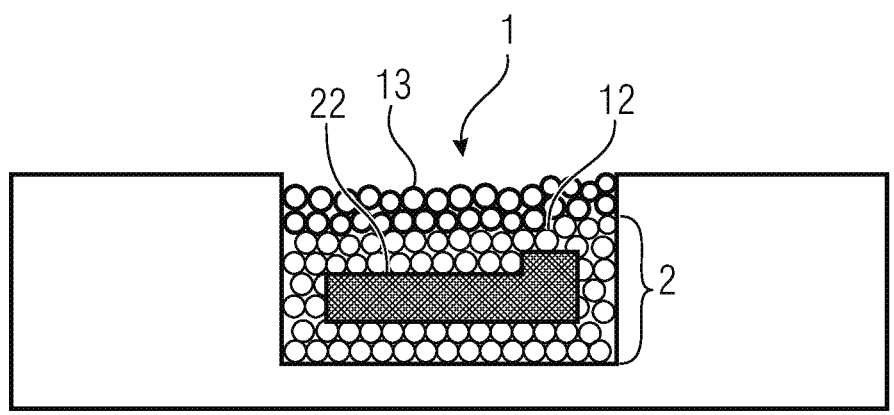

FIG. 2a shows a spherical molded body 21, for example, which is introduced into the recess 11 along with the multitude of loose particles 12. More specifically, the molded body 21 is located between the loose particles 12 of the second portion 2 of loose particles 12, whereas the first portion 1 of the particles 12 has solidified to form a porous structure 13. In FIG. 2b, for example, an L-shaped molded body 22 is depicted, which is introduced into the recess 11 along with the multitude of loose particles 12.

Advantageously, the molded body 21, 22 has a material different from that of the multitude of loose particles 12 contained within the recess 11. For example, the multitude of loose particles 12 may comprise a material which may be removed from the recess 11 by means of an etchant, whereas the material of the molded body 21, 22 does not react to the etchant. Thus, the multitude of particles 12 may be selectively removed from the recess, the molded body or molded bodies 21, 22 remaining within the recess 11.

Figure 3A:
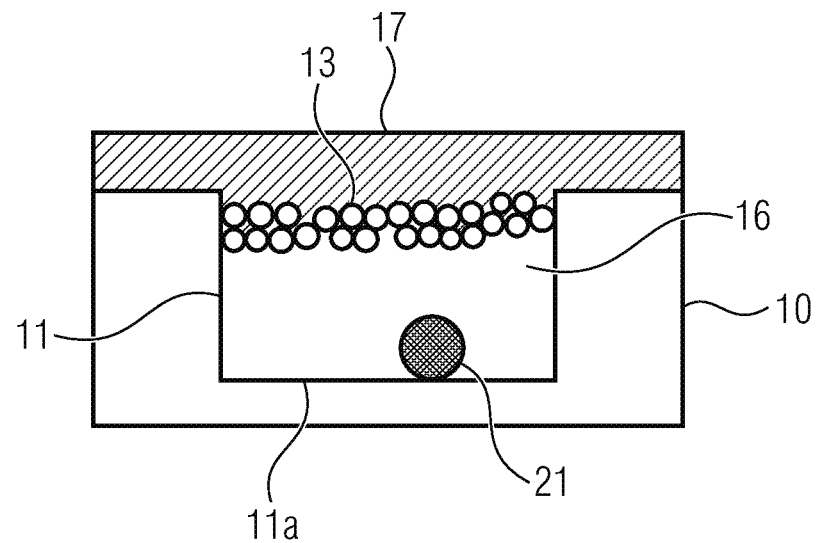
FIGS. 3a and 3b show a schematic representation for tilting of a device having a molded body enclosed inside the cavity.
Figure 3B:
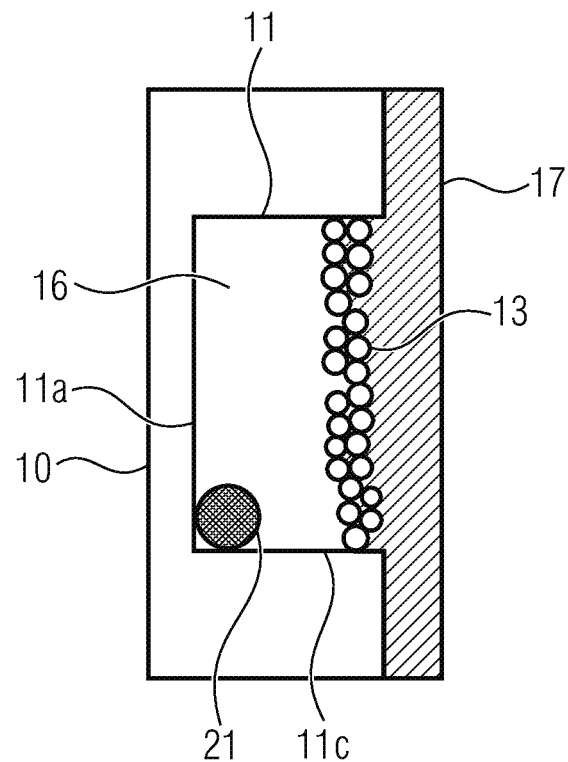

FIGS. 3a and 3b show a further embodiment in accordance with which the second portion 2 of the particles 12 located below the porous structure 13 has been removed. What remains is only the spherical molded body 21 previously described with reference to FIG. 2a. The molded body 21 is located within the cavity 16, which results as a consequence of removing the second portion 2 of the loose particles 12. The molded body 21 rests on the bottom 11a of the recess 11. In addition, the porous structure 13 is sealed off on its outer side by means of a coating 17.

FIG. 3b shows the device of FIG. 3a, however with a rightward tilt of 90°. Accordingly, the molded body 21 falls down, so that it rests, at least in portions, on the right-hand sidewall 11c of the recess 11. Moreover, the molded body 21 may abut, at least in portions, on the bottom 11a of the recess 11.

In such embodiments it may be useful to coat at least portions of the inner sides of the recess 11 (i.e. the bottom 11a and/or the sidewalls 11b, 11c) so as to reduce the adhesive forces and/or frictional forces of the inner sides 11a, 11b, 11c of the recess 11 toward the molded body 21. Likewise, it may be useful to apply a coating onto at least one inner side 11a, 11b, 11c of the recess 11, which coating reduces and/or shields off any radiation emanating from the molded body 21. This may be a metal layer, for example.

It may also be advantageous, for example, to line the inner sides 11a, 11b, 11c of the recess 11 with a layer prior to introducing the particles 12 and the molded bodies 21, 22 in accordance with FIG. 1b, said layer being deposited, e.g., by means of sputtering, CVD and other methods established in semiconductor technology. Said layer may be a layer, for example, which influences the adhesive and/or frictional behavior of the freely movable particles 12 or molded bodies 21, 22 on the inner sides 11a, 11 b, 11c of the cavity 11. Moreover, it may be a metallic layer so as to shield them off electromagnetically. It is also possible to apply a sequence of several layers which have the same or different functionalities.

As has just been explained with reference to FIGS. 3a and 3b, an object (particle 12b and/or molded body 21, 22) present within the cavity 16 may adopt a specific position within the cavity 16 as a function of the location of the substrate 10. A change in location may well be determined if the object 12b, 21, 22 present within the cavity 16 is an object having a magnetic property.

In accordance with an embodiment of the inventive method, an object (particle 12b and/or molded body 21, 22) is introduced, together with the loose particles 12a, into the recess, as is indicated in FIGS. 1b, 1c and 2a, 2b. Advantageously, the object 12b, 21, 22 is magnetized following removal of the part of the second portion of the loose particles 12a (FIGS. 1d, 3a, 3b).

Figure 4A:
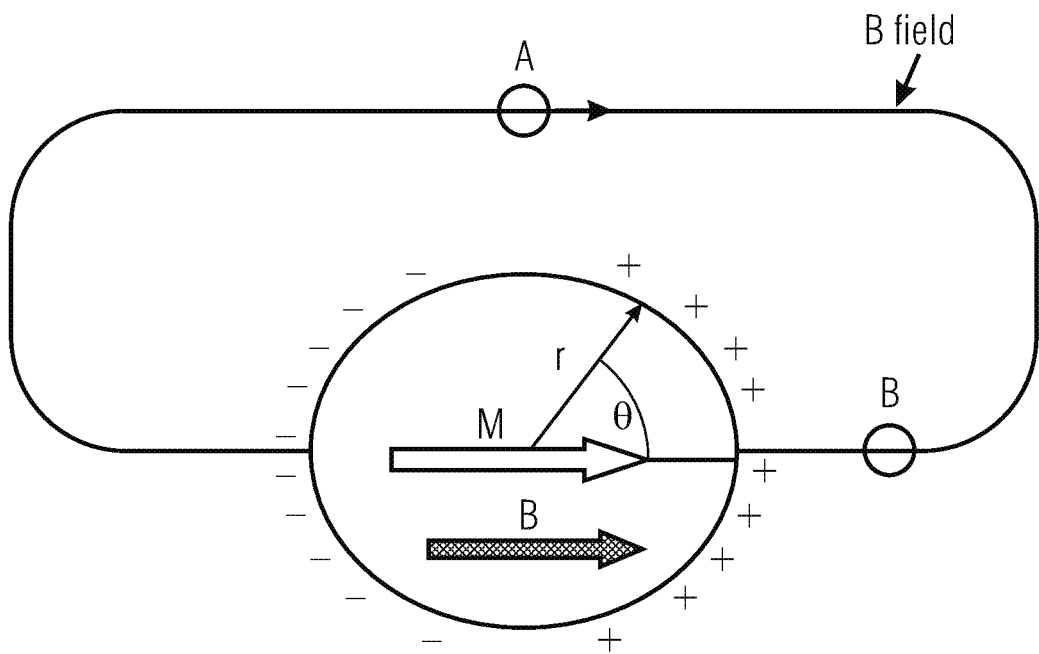
FIGS. 4a and 4b show the representation of the magnetic field strength of an NdFeB sphere as a function of its radius.
Figure 4B:
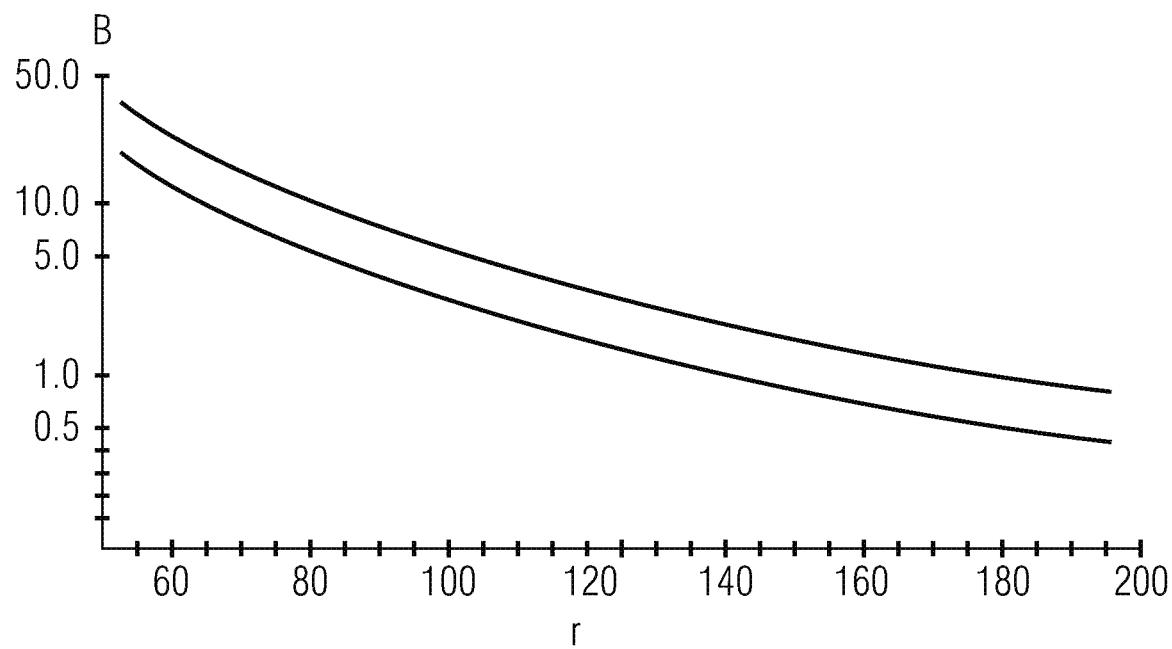

The particles 12b or the molded bodies 21, 22 may consist of any hard magnetic materials. As detectors, all known magnetic field sensors such as Hall, AMR or GMR sensors, as well as coils (inductances) may be considered. What is of particular interest are arrays consisting of magnetic field-sensitive components which enable a high level of positional resolution and may be manufactured by using CMOS-compatible processes, such as the so-called split-drain MOSFET (MAGFET), for example [1]. In [2] it is reported that the C-V characteristic of an "n-channel enhancement type MOSFET" changes by several percent under the influence of a magnetic field of 70 mT. As is shown in FIGS. 4a and 4b, comparable field strengths may already be generated by an NdFeB sphere having a radius of only 25 μm. Thus, transistors at a distance of 50 μm from the center of the sphere would be exposed, e.g., to fields of 20 to 50 mT. By comparison, the Earth's magnetic field is below 0.5 mT. FIGS. 4a and 4b depict the described magnetic field strength B as a function of the distance (radius) r for the magnetic field of an NdFeB sphere having a radius of 25 μm.

Given the above-mentioned findings, reference shall once again be made to FIGS. 3a and 3b. If freely movable magnetic particles 12b or molded bodies 21, 22 are located within the self-contained, e.g. hermetically sealed, cavity 16, and if this arrangement is combined with one or more suitable detectors arranged at a suitably small distance from the cavity 16, changes in the locations of the magnetic particles 12b or molded bodies 21, 22 within the cavity 16 may be determined which are caused, e.g., by vibration, shocks or tilting. The latter is illustrated by way of example in FIG. 3b. The particles 12b or molded bodies 21, 22 enclosed within the cavity 16 may react quite sensitively to movements of any kind if the cavity 16 is advantageously hermetically sealed while excluding humidity, and/or under vacuum, and in particular if it is additionally provided, on the inside 11a, 11b, 11c, with a coating for reducing adhesion. What is advantageous in this context is the fact that the particles 12b or molded bodies 21, 22 are mounted to be freely movable rather than being spring-mounted since in this manner, largely frequency-independent sensitivity may be ensured. In addition, structural sizes far below 1 mm³ and, therefore, very cheap components are possible.

Figure 5A:
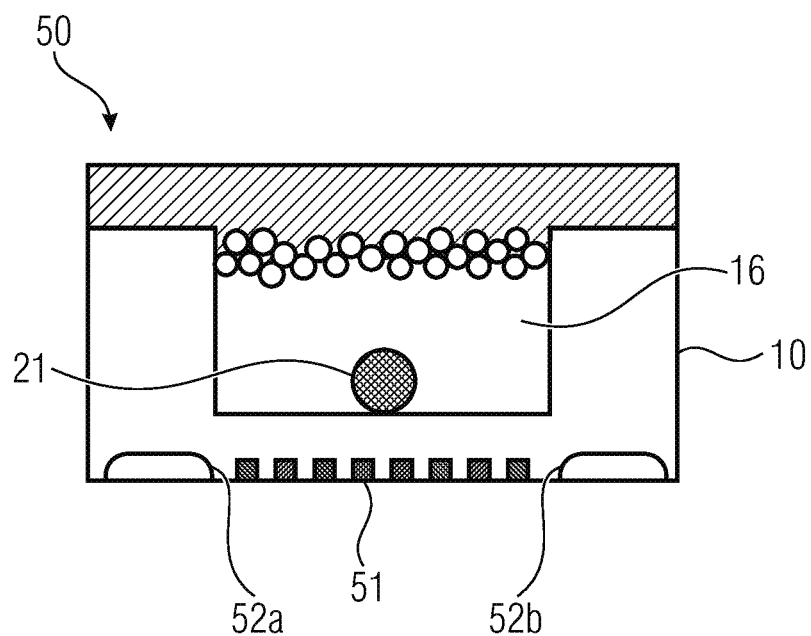
FIGS. 5a and 5b show a schematic representation of providing a magnetic field sensor system.
Figure 5B:
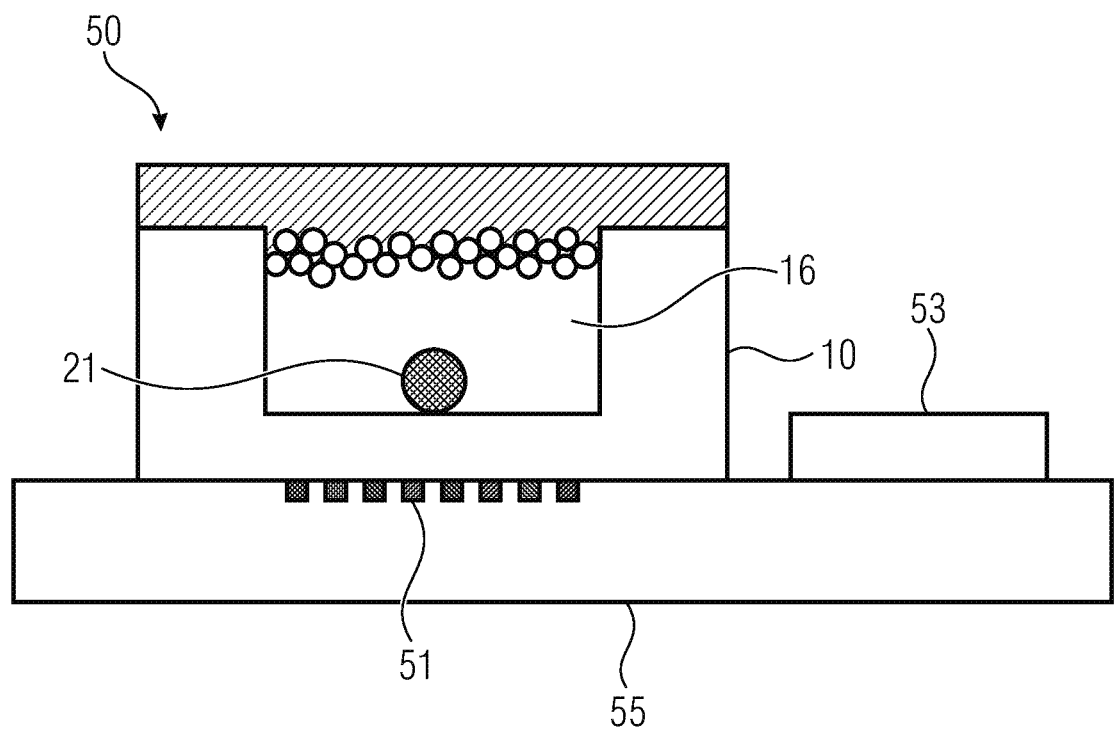

FIGS. 5a and 5b show embodiments of a motion sensor 50 comprising an individual, spherical magnetic molded body 21. Here, a magnetic field sensor system 51 is arranged at the substrate 10 which is configured to determine the magnetic field of the object (particle 12b and/or molded body 21, 22).

In FIG. 5a, the magnetic field sensor system 51 is implemented in an on-chip manner, i.e. the magnetic field sensor system 51 is formed within the substrate 10 such that the magnetic field sensor system 51 is arranged opposite an inner side 11a, 11b, 11c of the recess 11. In addition, an evaluation circuit 52a, 52b is configured in an on-chip manner, i.e. within the substrate 10. Thus, the magnetic field sensor system 51 is arranged directly at the substrate 10.

In FIG. 5b, the magnetic field sensor system 51 is arranged on a separate carrier 55. In addition, an evaluation circuit 53 is arranged on the separate carrier 55. Said separate carrier 55 is arranged at the substrate 10 such that the magnetic field sensor system 51 is arranged opposite an inner side 11a, 11b, 11c of the recess 11. Therefore, the magnetic field sensor system 51 is indirectly arranged at the substrate 10, i.e. by means of the separate carrier 55.

The magnetic field sensor system 51 may be a magnetic detector and/or a detector array, for example. In FIG. 5a, the detector (detector array) 51 and the evaluation electronics 52a, 52b are therefore integrated in an on-chip manner. In FIG. 5b, the sensor chip 10 is mounted on a separate carrier 55, which also carries the detector (detector array) 51 and the evaluation circuit 53. The detector (detector array) 55 and the evaluation circuit 53 are mounted on the separate carrier 55 in a hybrid manner here.

Figure 6A:
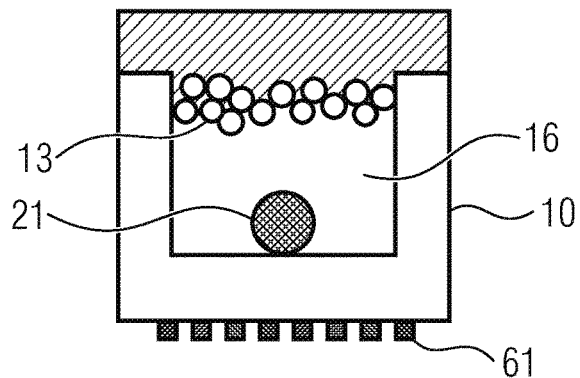
FIGS. 6a to 6c show a schematic representation of providing one or more coils and/or coil arrays.
Figure 6B:
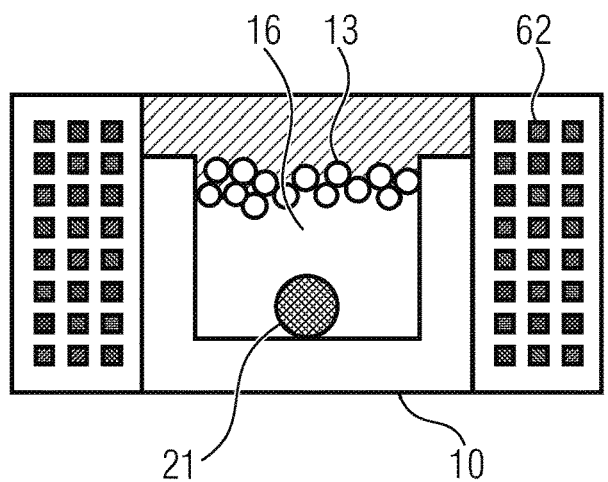
Figure 6C:
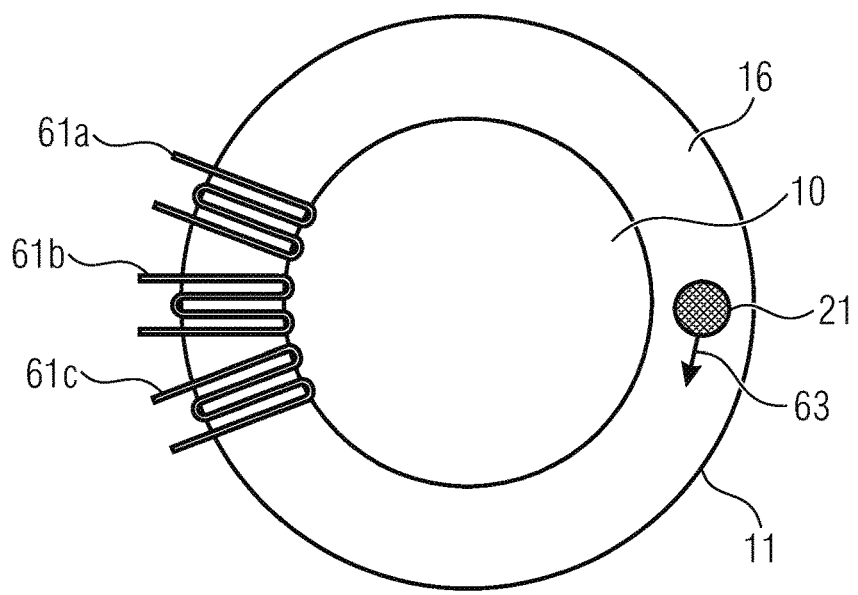

FIGS. 6a, 6b and 6c show off further embodiments, wherein one or more coils and/or one or more coil arrays are employed instead of the magnetic detectors 51 described above.

FIG. 6a depicts a further method step of the inventive method, in accordance with which a coil 61 interacting with the object (particle 12b and/or molded body 21, 22) is arranged at the substrate 10. By means of a relative movement between the coil 61 and the magnetic object (particle 12b and/or molded body 21, 22), an induced voltage is generated which is formed within the coil 61. The coil 61 may be implemented in an on-chip manner, i.e. within the substrate 10, i.e. the coil is arranged directly at the substrate 10.

FIG. 6b depicts a similar system, wherein a hybrid-mounted external coil, or coil array, 62 is arranged at the substrate 10 instead of the coil 61 integrated in an on-chip manner (FIG. 6a). The coil, or coil array, 62 is therefore indirectly arranged at the substrate 10.

The devices depicted in FIGS. 6a and 6b might be used, for the purpose of motion sensors, as non-resonant energy harvesters, for example, i.e. if a coil 61 or coil array 61 replaces the detector 51 or detector array 51 (FIGS. 5a, 5b). The two basic implementations comprising a three-dimensional coil 61 which is integrated in a one-sided manner, is planar or is hybrid-mounted, are schematically depicted in FIGS. 6a and 6b.

A further possible embodiment is depicted in FIG. 6c showing a top view of a substrate 10 having a recess 11. A magnetic spherical molded body (e.g. a permanent magnet) 21 may move in a circular manner within an annular recess, or cavity, 16 (see arrow 63) under the influence of a suitable excitation signal. In doing so, said molded body 21 successively passes a multitude of coils 61a, 61b, 61c which are arranged along the annular recess 11 and within which voltage pulses are induced as a result.

Generally, the inventive device may be configured as a MEMS component (microsystem). Since it is possible, in a MEMS component, to implement very small distances of few micrometers between the coil 61a, 61b, 61c and the magnet 21, the magnetic flux density to be expected is higher than in a comparable macroscopic setup. The cross-sectional area A of the coil and the number of windings N, however, are smaller than in a macroscopic setup.

In order to nevertheless generate comparable voltages, the magnetic flux density in a MEMS component would therefore have to be larger than in a macroscopic component by a factor of several 10.000. However, what is more realistic is a factor of 10 to 100. Thus, one obtains induced voltages (maximum open circuit voltage) in the order of magnitude of few millivolts. As far as power is concerned, one gains another factor of approx. 10 in a wire-wound resistor in a MEMS component due to the small number of windings. By cascading several coils with only one winding one may gain yet another factor of approx. 2 to 3. If one neglects impendence due to the low frequency, one may roughly estimate the power generated by means of $P=\frac{1}{8} U_{ind}^2 R$ with $R=R_{load}=R_{wire}$. Thus, a power of a maximum of approx. 1 mW results for the MEMS component in FIGS. 6a to 6c.

Figure 7A:
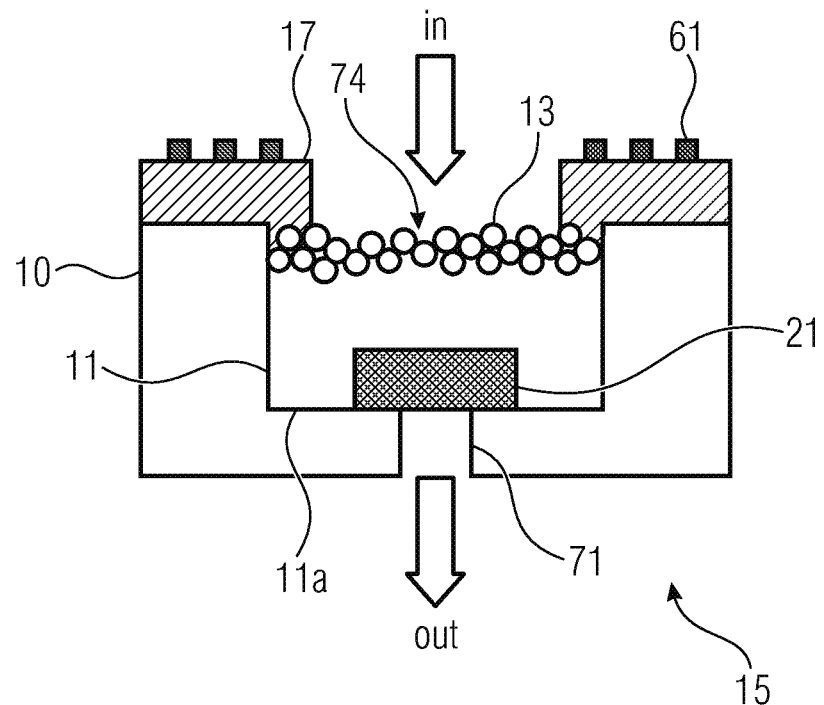
FIGS. 7a to 7c show a schematic representation of systems through which a fluid flows.
Figure 7B:
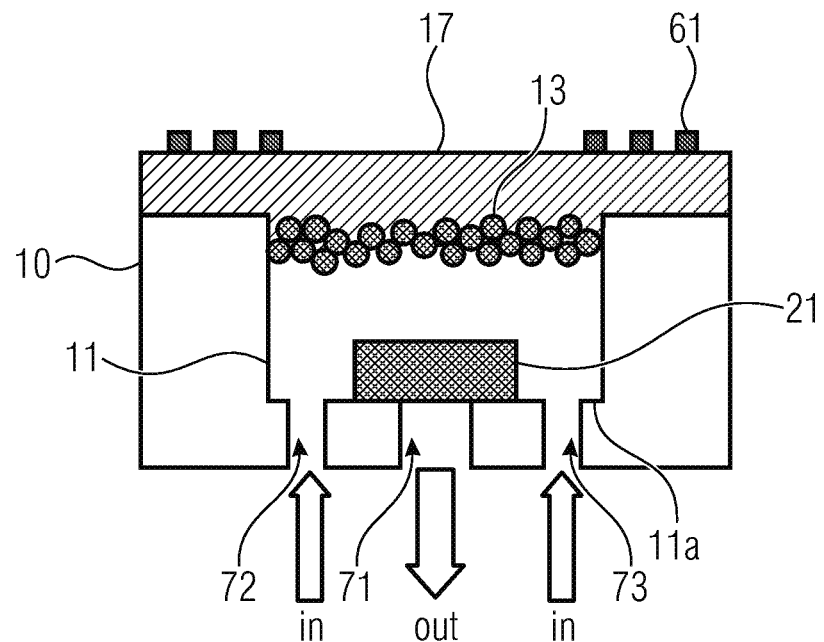
Figure 7C:
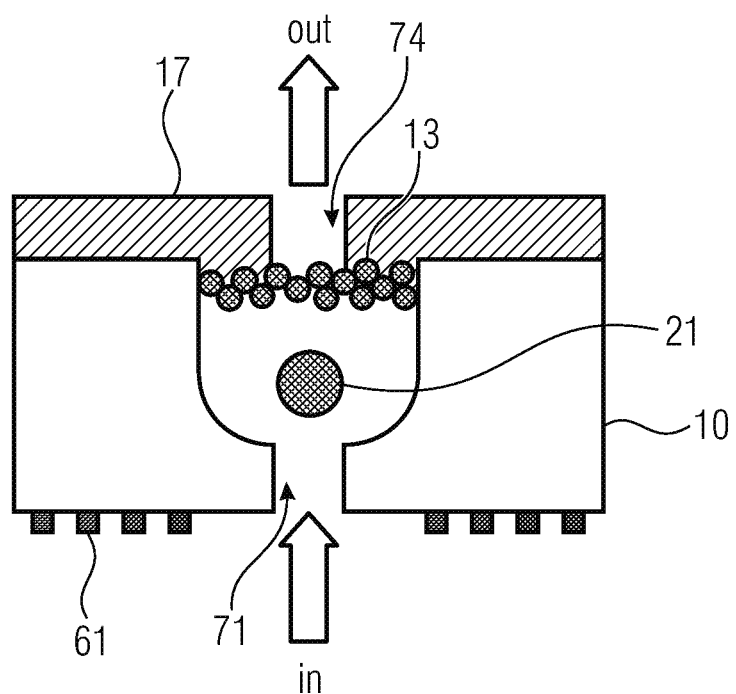

FIGS. 7a, 7b and 7c show further embodiments. FIG. 7a, for example, shows a step of the inventive method wherein an opening 71 is introduced into the substrate 10 in that side of the substrate 10 which is located opposite the porous structure 13, i.e. in the bottom 11a of the recess 11 provided within the substrate 10, said opening 71 providing a fluid connection between the recess 11 and its surroundings 15.

The cavity 16 formed between the porous structure 13 and the inner sides 11a, 11b, 11c of the recess 11 provided within the substrate 10 has a molded body 21 located therein. Here, the molded body 21 has an essentially rectangular shape.

As can be seen in FIG. 7a, the cross section of the opening 71 is smaller than the molded body 21, so that the opening 71 may be closed by means of the molded body 21 so as to suppress any fluid connection to the surroundings 15.

FIG. 7b shows a similar embodiment, wherein two further openings 72, 73 are introduced into the substrate 10, all three openings 71, 72, 73 providing a fluid connection between the recess 11 and the surroundings 15. In the embodiment depicted in FIG. 7b, a passivation layer 17 is additionally applied onto the porous structure 13, as was described above, said passivation layer 17 extending across the entire porous structure 13.

In FIG. 7a, however, there is also a passivation layer 17 which has been applied onto the porous structure 13. However, the passivation layer 17 extends only across portions of the porous structure 13. An area, or a portion, 74 in the center of the porous structure 13 does not have the passivation layer 17 applied to it.

In the previous embodiments, therefore, the particles 12b and/or molded bodies 21, 22 enclosed within the cavity 16 were insulated from the surroundings 15 by a passivation layer 17 (FIG. 1d). As is shown in FIG. 7b, however, it may also be advantageous to allow the ambient medium to flow through the cavity 16. To this end, sealing of the cavity 16 may be dispensed with, or one may cover only portions of the porous structure 13 with the passivation layer 27 in portions only.

Alternatively, new access openings 74 may also be generated once the structure of FIGS. 1a to 1e has been completed, e.g. by means of etching the substrate 10 and/or the sealing and/or passivation layer 17.

One application would involve microvalves, for example. Two possible embodiments are schematically depicted in FIGS. 7a and 7b. For the simple implementation in FIG. 7a, a coil 61 and, for coupling the medium of the surroundings 15, two openings 71, 74 may be generated within the substrate 10 and/or within the sealing layer 17 in addition to the manufacturing process described in FIGS. 1 to 1e. The molded body 21 closes the lower opening 71 formed in the substrate 10 and thus provides a valve functionality.

In the idle state, i.e. in the state without any energy supply, the valve 21, 71 is closed. The fluid entering through the upper entry opening 74 formed in the passivation layer 17 (designated by "in") presses the magnetic molded body 21 against the lower exit opening 71 (designated by "out"). If electric current flows through the coil 61, the molded body 21 will be pulled upward, i.e. toward the passivation layer 17, and will unblock the lower exit opening 71. The coil 61 may be actuated permanently so as to keep the valve 21, 71 open.

In the embodiment of FIG. 7b, the porous structure 13 comprises a magnetic material. Here, the solidified porous structure 13 consists of soft or hard magnetic particles 12. In principle, the multitude of loose particles 12 arranged within the cavity 16 prior to being removed may include particles which comprise a magnetic material. The porous structure 13 which is formed by means of the coating process will then comprise these very magnetic particles, so that the porous structure 13 itself will have magnetic properties.

In the case of hard magnetic particles, they may be magnetized together with the magnetic molded body 21. As is the case in the embodiment of FIG. 7a, the valve 21, 71 formed from the molded body 21 and from the opening 71, which may be closed by means of the molded body 21, is closed in the idle state. Fluid entering through the entry openings 72, 73 (designated by "in") presses the magnetic molded body 21 against the exit opening 71 (designated by "out").

If electric current flows through the coil 61, the molded body 21 will be pulled upward, i.e. toward the porous structure 13, and will thus unblock the exit opening 71. Due to the magnetic attraction between the porous structure 13 comprising magnetic particles, on the one hand, and the molded body 21, on the other hand, the latter will remain on the lower side of the porous structure 13 even after the coil 61 has been switched off.

For closing the valve 21, 71, the coil 61 is controlled with reversed polarity so as to generate repulsive electromagnetic forces. If they are sufficiently large, the molded body 21 will detach from the porous structure 13 and will close the exit opening 71 again. Due to the pressure difference which is building up between "in" and "out", the molded body 21 will remain in this position without any further energy supply.

In the embodiments shown in FIGS. 7a and 7b, an externa hybrid-mounted coil may just as well be used instead of an integrated coil. In addition, the shapes and sizes of the recess 11 and of the magnetic molded body 21, the arrangement of the coils 61 as well as the location and number of the entry and exit openings 71, 72, 73, 74 may vary.

FIG. 7c shows a further embodiment. Here, the substrate 10 also comprises an opening 71 provided on that side of the substrate 10 which is located opposite the porous structure 13. As compared to FIGS. 7a and 7b, this opening 71 is an entry opening, however, and is therefore designated by "in".

The passivation layer 17, in turn, leaves a portion of the porous structure 13 free. In this manner, an opening 74 is formed which now is an exit opening, however, as compared to FIGS. 7a and 7b and is therefore designated by "out".

The cavity 16 has a spherical molded body 21 located therein which is larger than the cross section of the opening 71 provided within the substrate 10, so that the molded body 21 can close the opening 71. This, in turn, provides a valve functionality.

In the embodiment shown in FIG. 7c, a further application in the form of a flow sensor or flow controller would also be feasible, for example. In this case, too, at least one coil 61 is generated and openings 71 are produced within the substrate 10 and/or in the sealing layer 17 in addition to the process depicted in FIGS. 1a to 1d.

If a fluid flows upward (i.e. from the bottom 11a of the recess 11 toward the porous structure 13) through the recess 11, or through the cavity 16, the magnetic molded body 21 will be pressed, or made to be suspended, upward (i.e. toward the porous structure 13).

The change in location of the magnetic molded body 21 results in a change in inductance and/or a change in the resonant frequency of the coil 61, which may be readily measured by means of a weak, high-frequency AC signal. Irrespective thereof, the location of the magnetic molded body 21 may be influenced by means of a direct current flowing through the same coil 61, whereby flow control is also made possible.

As was discussed above with reference to FIGS. 7a to 7c, it may therefore be advantageous to not completely seal off the cavity 16 by means of the passivation layer 17, or to generate new openings 71, 72, 73, 74 within the substrate 10 or the sealed-off porous structure 13 after the very sealing process so as to enable a liquid or gaseous medium to flow into and/or through the cavity 16, and to enable interaction with the particles 12 or molded bodies 21, 22 enclosed therein.

Figure 8A:
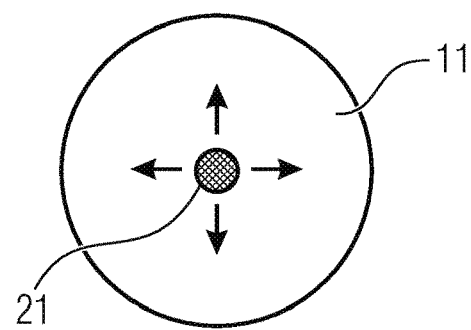
FIGS. 8a to 8d show embodiments of different implementations of the recess provided within the substrate.

FIGS. 8a to 8d show possible implementations of recesses 11 to be introduced into the substrate 10. FIG. 8a shows a recess 11 comprising a complete circular implementation. The circular recess 11 has a molded body 21 arranged therein which is able to move in any direction (see motion arrows).

Figure 8B:
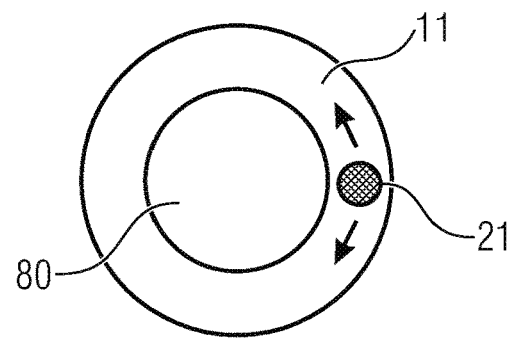

FIG. 8b shows a further circular implementation of the recess 11, said recess 11 not being free from interruptions. Said recess is formed in the shape of a toroid, or a donut, wherein only the outer circumference of the recess 11 forms a depression within which the molded body 21 may move (see motion arrows). The center 8 has no recess formed therein. Said part will typically be formed from the substrate material.

Figure 8C:
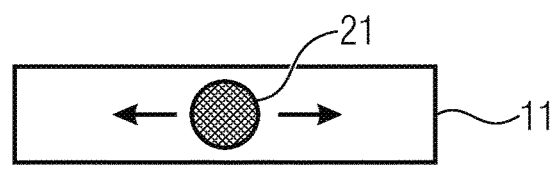

FIG. 8c shows an elongated recess 11. Here, the recess 11 has the shape of a rectangle. The molded body 21 located therein may move along the rectangle (see motion arrows).

Figure 8D:
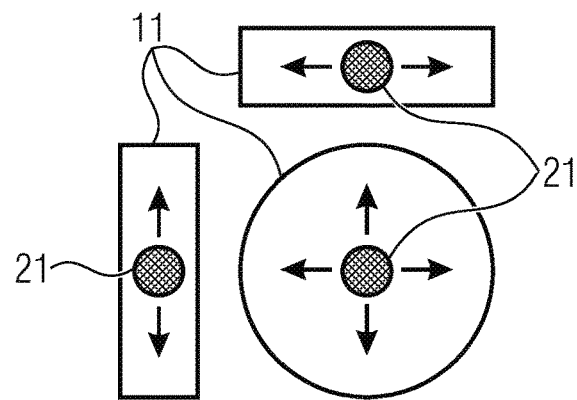

FIG. 8d shows a combination of the above-described shapes of recesses 11 with molded bodies 21 arranged therein.

As was already mentioned above, the magnetic particles 12 and/or molded bodies 21, 22 may be processed in the demagnetized state and may be magnetized only toward the end of the manufacturing process at a position suitable for this purpose, for example prior to etching out the particles 12a comprising material A.

However, said magnetizing process may also be performed not until the particles 12a comprising material A have been etched out. If, e.g., a passivation layer is applied following said etching-out process, e.g. by means of PECVD at 300° C., the magnetization process carried out previously would be lost and would have to be repeated.

The recess 11 etched, in accordance with FIG. 1a, at the beginning of the manufacturing process may have most varied shapes, depending on the application. FIGS. 8a to 8d show several fundamental possibilities. To ensure uniform sensitivity within the plane, a disk or donut shape (FIGS. 8a and 8b, respectively) is particularly suitable. However, elongate arrangements may also be of interest if movements or accelerations in specific directions are to be detected (FIG. 8c). In addition, several sensor elements may be combined with recesses 11 of different geometries within a sensor array (FIG. 8d).

A possible field of application of the embodiments previously described in all of the figures are motion sensors of any kind, for example. In the simplest case, they are, e.g., wake-up sensors for activating electronic circuits and devices, or sensors for detecting body movements, e.g. pedometers. A further field of application is sensing of low-frequency and/or non-periodic oscillations or vibrations which signal, e.g., wearing effects on machine parts. However, accelerations may also be detected if a sufficiently high resolution of the positions and/or of the trajectories of the magnetic particles 12b or molded bodies 21, 22 within the cavity 16 can be ensured.

Further feasible implementations would be electromagnetic energy harvesters, for example, which exploit mechanical energy. In the simplest case, they are based on a spring-mounted mass, the mechanical oscillation of which, excited by an external, periodic vibration, is transformed to electric energy, e.g. while using the electromagnetic or piezoelectric principle. However, such systems will only function effectively if the excitation vibration is close to the resonant frequency of the movable mass. Electromagnetic vibration harvesters of this kind which have been produced conventionally have been on offer, e.g., for frequencies from 25 to 120 Hz [3].

With micromechanical resonant harvesters, the operating range is mostly above 50 Hz. It is technologically difficult to implement lower resonant frequencies due to the limited mass of a MEMS structure. What is more, the vibrations occurring within said low-frequency range are mostly non-periodic. Consequently, a large range of the available vibration sources (human motion, civil infrastructure, buildings, cars, etc.) remains unexploited [4].

Improved effectiveness within the low-frequency range is achieved when the movable mass, once it has been deflected, is able to post-oscillate in a resonant manner. An example thereof is the electromagnetic PFIG harvester described in [5]. It contains a magnet which may be moved to and fro between two stable positions by sufficiently large impacts. In each of said positions, a further magnet is made to oscillate by the mechanical impulse given during switching, as a result of which a current is induced in a coil. Further bistable systems based on permanent magnets are described in [6], for example.

An alternative to the resonant systems is presented by harvesters, the mass of which is freely movable, i.e. wherein suspension is completely missing. The main advantage consists in that said harvesters function equally effectively not only within a narrow band around the resonant frequency, but across a wide frequency range. An example is the electromagnetic harvester, described in [7], for supplying energy to car keys, which consists of a permanent magnet which may freely move between two conventional circuit boards having coils. As a function of the geometry of the coils and of the size of the magnet, the voltage induced was 1.1 V at the maximum. Generally, one has observed a considerable decrease in the voltage induced as the size of the magnet decreased. Comparable MEMS components have not yet been presented.

The motion sensors depicted in FIGS. 5a and 5b might be used as non-resonant harvesters as defined by the above-mentioned examples if a coil 61 or a coil array 62 (see FIGS. 6a and 6b) replaces the detector or detector array 51. The two basic implementations comprising a three-dimensional coil which is integrated on one side, is planar and/or hybrid-mounted, are shown in FIGS. 6a and 6b and have already been described. However, it would not be very useful to transfer the arrangement of [7] as it is to a MEMS component. Due to the limited number of windings of a planar coil alone, the voltage induced would be much smaller than it is in [7].

In summary, it shall once again be mentioned that one aspect of the present invention is based on the fact that the particles 12b of molded bodies 21, 22 in accordance with FIG. 1d, which are located below the porous structure 13 and have remained uncoated, may be selectively etched out through the porous structure 13. This results in a cavity 16 within the substrate 10, which cavity 16 is limited by the solidified porous structure 13 on the upper side and by the substrate material on the other sides. If a mixture of particles 12, containing particles 12a of material A and particles 12b of material B, has been introduced into the recess 11, those particles 12a of material A which have remained uncoated may be etched out selectively with respect to those particles 12b of material B which have remained uncoated. The latter remain within the cavity 16 and below the porous structure 13, where they can move freely. The inventive approach is schematically depicted in FIGS. 1a to 1d.

A cavity and/or recess 11 of FIG. 1a, which is provided within the substrate 10, has a multitude of particles 12, i.e. a mixture of particles 12a, 12b of materials A and B, introduced into it (FIG. 1b). Now the particles 12 are solidified in the upper area by means of ALD deposition (FIG. 1c), cavities within the solidified particles 12 being maintained to a very large degree.

The particles 12a of material A are now etched through the porous structure 13 selectively with respect to the particles 12b of material B. The latter remain within the cavity 16 underneath the porous structure 13, where they may move, depending on how much space has been created by etching out the particles 12a of type A (FIG. 1d). By applying a layer 17 onto the porous membrane 13, the cavity 16 comprising the particles 12b of material B may be closed (FIG. 1c), if need be in a hermetical manner under vacuum or in a specific atmosphere.

The material B may be represented not only by particles 12b, but generally also by individual or several three-dimensional bodies 21, 22 of different numbers, shapes and sizes, provided that they fit into the (e.g. etched) cavity and/or recess 11 (see FIGS. 2a and 2b). The molded bodies 21, 22 or particles 12b of material B may be mixed with the particles 12a of material A before the cavity 11 is filled. However, they may also be successively introduced into the cavity 11, e.g. if the molded body 12b of material B is very large. The method may be extended to more than two materials, i.e. in the event of there being several molded bodies 21, 22, they may consist of different materials B, C, D etc., and/or the particles 12 introduced may be a mixture consisting of materials A to C.

The approach of FIGS. 1 to 1e enables enclosing of three-dimensional bodies 21, 22 of most varied numbers, shapes and sizes, individual, relatively large entities as well as a multitude of small particles 12 within defined cavities 16 within a substrate 10.

The three-dimensional bodies 21, 22 are freely movable within the cavities 16. The locations or arrangements, sizes or shapes, chemical/physical properties or compositions of the three-dimensional bodies 21, 22 may change under the influence of, e.g.:

a) external electromagnetic fields and/or radiations of any kind, or
b) temperature, or
c) movements and/or accelerations or gravitation, or
d) a medium which enters into the self-contained cavity 16 and/or flows through same, e.g. through the porous structure 13 and/or through separately generated openings 71, 72, 73, 74.

This may be exploited for various sensor or actuator arrangements.

A device in accordance with previously described embodiments may further comprise an electrode structure which is contacted with the first portion and/or the second portion of particles and is configured to apply or sense an electric potential between electrodes of the electrode structures, which means that an electric potential present at or between the particles may be generated or sensed.

Embodiments previously describes are independent of a size (e.g. diameter or lateral dimension). If the particles 12 are configured as aluminum oxide particles (splitters), for example, the latter may have diameters of, e.g., between 1 and 20 µm, 2 and 15 µm or between 5 and 12 µm. For example, if silicone particles are used, they may have diameters or lateral dimensions ranging from 0.1 µm to 20 µm, from 0.5 µm to 5 µm, or from 0.8 µm to 1,2 µm.

Even though embodiments described above have been described such that the porous structure 13 comprises cavities which are at least partly connected to one another, so that the porous structure 13 forms a porous membrane, one may also achieve, in particular with a particle size of <2 µm, by means of the coating process, that the porous structure 13 is sealed off, i.e. that the cavities between the particles 12 are closed. In this manner, it is also possible to close a recess 11 by means of the coating.

Even though embodiments described above have been described such that the substrate 10 comprises a planar shape, the substrate 10 may also have other shapes. For example, the substrate 10 may have a curved shape (for example, a dome structure) of a shape which in portions is planar and/or bent.

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described within the context of or as a method step also represent a description of a corresponding block or detail or feature of a corresponding device.

The method steps described may also be performed in any order other than that indicated in the claims.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention may further be implemented in the following embodiments:

1. Method of producing a device, comprising:
    providing a substrate (10) comprising a recess (11);
    introducing a multitude of loose particles (12) into the recess (11);
    coating a first portion (1) of the particles (12), so that the first portion (1) is connected to form a solidified porous structure (13), while using a coating process comprising a depth of penetration which extends from an opening (11*d*) of the recess (11), along a direction of depth (14), and into the recess (11);
    wherein the depth of penetration of the coating process into the recess (11) is set such that a second portion (2) of the particles (12) is not connected by means of the coating, so that the solidified first portion (1) of the particles (12) is arranged between the second portion (2) of the particles (12) and surroundings (15) of the recess (11); and
    at least partly removing the second portion (2) of the particles (12) from the recess (11).
2. Method of embodiment 1, wherein at least 10%, advantageously at least 25%, and more advantageously more than 50% of the second portion (2) of the particles (12) are removed from the recess (11).
3. Method of embodiment 1 or 2, wherein the second portion (2) of the particles (12) is completely removed from the recess (11).
4. Method of any of the previous embodiments, wherein the second portion (2) of the particles (12) is removed by means of an etching process.
5. Method of any of the previous embodiments, wherein the first portion (1) of the particles (12) comprises a material different from that of the second portion (2) of the particles (12).
6. Method of any of the previous embodiments, wherein loose particles (12*a*) comprising a first material (A) and subsequently, loose particles comprising a second material (C) are first introduced into the recess (11), and wherein the particles comprising the second material (C) are subsequently coated.
7. Method of any of the previous embodiments, wherein a coating (17), in particular a passivation layer, is applied onto the porous structure (13), so that the coating (17) extends at least in portions across the substrate (10) and/or extends at least in portions across the porous structure (13).
8. Method of embodiment 7, wherein the coating (17) is applied onto the porous structure (13) such that it covers the entire porous structure (13) and seals it off in a fluid-tight manner.
9. Method of any of the previous embodiments, wherein at least one inner side (11*a*, 11*b*, 11*c*) of the recess (11) has applied onto it, at least in portions, a layer which reduces adhesive forces and/or frictional forces between the recess (11) and an object (12*b*, 21, 22) which remains within the recess (11) after the second portion (2) of the particles (12) has been at least partly removed, and/or a layer which reduces the radiation emanating from an object (12*b*, 21, 22) which remains within the recess (11) after the second portion (2) of the particles (12) has at least been partly removed.
10. Method of any of the previous embodiments, wherein the plurality of loose particles (12) comprise particles (12*a*, 12*b*) comprising magnetic materials.
11. Method of any of the previous embodiments, wherein the coating process by means of which the first portion (1) of the particles (12) is coated is an ALD (atomic layer deposition) process.
12. Method of any of the previous embodiments, wherein, prior to coating of the first portion (1) of the particles (12), at least one object (12*b*, 21, 22) is introduced into the recess (11) in addition to the multitude of loose particles (12).
13. Method of embodiment 12, wherein the at least object is a particle (12*b*) comprising a material different from that of the multitude of loose particles (12), or wherein the at least one object is a molded body (21, 22) comprising a material different from that of the multitude of loose particles (12).
14. Method of embodiment 12 or 13, wherein the at least one object (12*b*, 21, 22) comprises a magnetic property.
15. Method of embodiment 14, wherein the at least one object (12*b*, 21, 22) is introduced into the recess (11) in a demagnetized state and is magnetized prior to or following the at least partial removal of the second portion (2) of the particles (12).
16. Method of embodiment 14 or 15, wherein a magnetic field sensor system (51) is arranged on the substrate (10) so as to determine the magnetic field of the at least one object (12*b*, 21, 22) by means of the magnetic field sensor system (51).
17. Method of any of embodiments 14 to 16, wherein a coil (61, 62) interacting with the at least one object (12*b*, 21, 22) is arranged at the substrate (10) so as to generate, by means of a relative movement between the coil (61, 62) and the at least one object (12*b*, 21, 22), an induced voltage which forms within the coil (61, 62), or to exert a magnetic induction force on the at least one object (12*b*, 21, 22) by means of an electric current flowing through the coil (61, 62).
18. Method of any of the previous embodiments, wherein an opening (71) is introduced into the substrate (10) in that side (11*a*) of the substrate (10) which is located opposite the porous structure (13), said opening (71) providing a fluid connection between the recess (11) and the surroundings (15).
19. Method of embodiment 18, wherein the cross section of the opening (71) is smaller than an object (12*b*, 21, 22) which remains within the recess (11) once the second portion (2) of the particles (12) has been at least partly removed, so that the opening (71) may be closed by means of the object (12*b*, 21, 22) so as to suppress the fluid connection to the surroundings (15).
20. Method of any of the previous embodiments, wherein said provision of the substrate (10) includes providing a substrate (10) having a circular recess and/or an elongated recess.
21. Device comprising
    a substrate (10) comprising a recess (11), and
    a porous structure (13) which is arranged within or at the recess (11) such that a cavity (16) remains between the recess (11) and the porous structure (13),
    wherein the porous structure (13) comprises a multitude of particles (12*a*) which are connected to one another by means of a coating and are solidified to form the porous structure (13), and
    wherein less than 90% of the volume of the cavity (16) is filled with loose particles (12*a*).
22. Device of embodiment 21, wherein less than 75%, advantageously less than 50%, more advantageously less than 25%, and particularly advantageously less than 10% of the volume of the cavity (16) is filled with the loose particles (12a), or wherein the cavity (16) comprises none of said loose particles (12a).

23. Device of embodiment 21 or 22, wherein the loose particles (12) located within the cavity (16) comprise a material different from that of the particles (12) solidified to form the porous structure (13).

24. Device of any of embodiments 21 to 23, wherein the cavity (16) has at least one object (12b, 21, 22) arranged therein, said at least one object being a particle (12b) comprising a material (B) different from the material (A) of the loose particles (12a) present within the cavity (16), or wherein said at least one object is a molded body (21, 22) comprising a material different from that of the loose particles (12) present within the cavity (16).

25. Device of embodiment 24, wherein the at least one object (12b, 21, 22) comprises a magnetic property.

26. Device of embodiment 25, wherein a magnetic field sensor system (51) is arranged at the substrate (10) and is configured to determine the magnetic field of the at least one object (12b, 21, 22).

27. Device of any of embodiments 25 or 26, wherein a coil (61, 62) interacting with the at least one object (12b, 21, 22) is arranged at the substrate (10) and is configured to generate, by means of a relative movement between the coil (61, 62) and the at least one object (12b, 21, 22), an induced voltage which forms within the coil (61, 62), or to exert a magnetic induction force on the at least one object (12b, 21, 22) by means of an electric current flowing through the coil (61, 62).

28. Device of any of embodiments 21 to 27, wherein the porous structure (13) comprises a multitude of particles (12) having a magnetic property.

29. Method of any of embodiments 21 to 28, wherein a coating (17), in particular a passivation layer, is applied onto the porous structure (13), so that the coating (17) extends at least in portions across the substrate (10) and/or extends at least in portions across the porous structure (13).

30. Method of embodiment 29, wherein the coating (17) covers the entire porous structure (13) and seals it off in a fluid-tight manner.

31. Device of any of embodiments 21 to 30, wherein an opening (71) is formed within the substrate (10) in that side (11a) of the substrate (10) which is located opposite the porous structure (13), said opening (71) providing a fluid connection between the recess (11) and the surroundings (15).

32. Device of embodiment 31, wherein the cross section of the opening (71) is smaller than an object (12b, 21, 22) located within the cavity (16), so that the opening (71) may be closed by means of the object (12b, 21, 22) so as to suppress the fluid connection to the surroundings (15).

33. Device of any of embodiments 21 to 32, wherein the substrate (10) comprises a circular recess and/or an elongated recess.

SOURCES

[1] J. J. Clark, "CMOS magnetic sensor arrays", Proc. IEEE Solid-State Sensor and Actuator Workshop, Hilton Head, USA, 1988

[2] A. Achayya et al., "Experimental study on the effect of magnetic field on current-voltage characteristics of n-channel enhancement-type MOSFET", Journal of Electron Devices, Vol. 13, 2012, pp. 945-948

[3] http://www.perpetuum.com/products/vibration-energy-harvester.asp

[4] K. Najafi et. al., "Microsystems for energy harvesting", Proc. IEEE Transducers '11, Beijing, China, June 5-9, 2011

[5] T. Galchev et al., "Non-resonant bi-stable frequency-increased power scavenger from low-frequency ambient vibration", Proc. IEEE Transducers 2009, Denver, Col., USA, June 21-25, 2009

[6] B. Ando et al., "Nonlinear mechanism in MEMS devices for energy harvesting applications", J. Micromech. Microeng. 20 (2010) 125020 (12pp)

[7] X. Li et al., "Li Non-resonant electromagnetic energy harvester for car-key applications", PowerMEMS 2013, Journal of Physics: Conference Series 476 (2013) 012096

The invention claimed is:

1. A method of producing a device, comprising:
providing a substrate comprising a recess;
introducing a multitude of loose particles into the recess;
coating a first portion of the particles, so that the first portion is connected to form a solidified porous structure, while using an ALD (atomic layer deposition) coating process comprising a depth of penetration which extends from an opening of the recess, along a direction of depth, and into the recess;
wherein the depth of penetration of the coating process into the recess is set such that a second portion of the particles is not connected by means of the coating, so that the solidified first portion of the particles is arranged between the second portion of the particles and surroundings;
selectively removing from the recess, at least partly, the second portion of the particles which is enclosed and has remained uncoated, while maintaining the solidified porous structure comprising the connected first portion of the particles, thereby forming a cavity between the recess provided within the substrate and the first portion of the particles which has solidified to form the porous structure; and
wherein the second portion of the particles comprises a first type of particles comprising a first material and a second type of particles comprising a different second material, and wherein a specific one of said two types of particles is selectively removed by means of a suitable etchant, while the particles of the other one of said two types of particles remain inside the cavity and freely move therein.

2. The method as claimed in claim 1, wherein at least 10% of the second portion of the particles are removed from the recess.

3. The method as claimed in claim 1, wherein the second portion of the particles is completely removed from the recess.

4. The method as claimed in claim 1, wherein the second portion of the particles is selectively removed by means of an etching process which uses an etchant suitable for selectively removing the second portion of the particles while maintaining the porous structure.

5. The method as claimed in claim 1, wherein a coating, in particular a passivation layer, is applied onto the porous structure, so that the coating extends at least in portions across the substrate and/or extends at least in portions across the porous structure.

6. The method as claimed in claim 5, wherein the coating is applied onto the porous structure such that it covers the entire porous structure and seals it off in a fluid-tight manner.

7. The method as claimed in claim 1, wherein at least one inner side of the recess has applied onto it, at least in portions, a layer which reduces adhesive forces and/or frictional forces between the recess and an object which remains within the recess after the second portion of the particles has been at least partly removed, and/or a layer which reduces the radiation emanating from an object which remains within the recess after the second portion of the particles has at least been partly removed.

8. The method as claimed in claim 1, wherein the plurality of loose particles comprise particles comprising magnetic materials.

9. The method as claimed in claim 1, wherein an opening is introduced into the substrate in that side of the substrate which is located opposite the porous structure, said opening providing a fluid connection between the recess and the surroundings.

10. The method as claimed in claim 1, wherein said provision of the substrate comprises providing a substrate comprising a circular recess and/or an elongated recess.

11. A method of producing a device, comprising:
providing a substrate comprising a recess;
introducing a multitude of loose particles into the recess;
coating a first portion of the particles, so that the first portion is connected to form a solidified porous structure, while using an ALD coating process comprising a depth of penetration which extends from an opening of the recess, along a direction of depth, and into the recess;
wherein the depth of penetration of the coating process into the recess is set such that a second portion of the particles is not connected by means of the coating, so that the solidified first portion of the particles is arranged between the second portion of the particles and surroundings;
selectively removing from the recess, at least partly, the second portion of the particles which is enclosed and has remained uncoated, while maintaining the solidified porous structure comprising the connected first portion of the particles, thereby forming a cavity between the recess provided within the substrate and the first portion of the particles which has solidified to form the porous structure,
wherein, prior to coating of the first portion of the particles, at least one object formed as a molded body is introduced into the recess in addition to the multitude of loose particles, and
wherein after the step of selectively removing, at least partly, the second portion of the particles from the recess, the molded body enclosed within the cavity may freely moves therein.

12. The method as claimed in claim 11, wherein the at least one object comprises a material different from that of the multitude of loose particles, wherein the multitude of loose particles comprise a material which is removed from the recess by means of an etchant, whereas the material of the at least one object does not react to the etchant.

13. The method as claimed in claim 11, wherein the at least one object comprises a magnetic property.

14. The method as claimed in claim 11, wherein the at least one object is introduced into the recess in a demagnetized state and is magnetized prior to or following the selective removal of the second portion of the particles.

15. The method as claimed in claim 14, wherein a magnetic field sensor system is arranged on the substrate so as to determine the magnetic field of the at least one object by means of the magnetic field sensor system.

16. The method as claimed in claim 11, wherein a coil interacting with the at least one object is arranged at the substrate so as to generate, by means of a relative movement between the coil and the molded body, an induced voltage which forms within the coil, or to exert a magnetic induction force on the at least one object by means of an electric current flowing through the coil.

17. The method as claimed in claim 11, wherein an opening is introduced into the substrate in that side of the substrate which is located opposite the porous structure, said opening providing a fluid connection between the recess and the surroundings.

18. The method as claimed in claim 11, wherein in that side of the substrate which is located opposite the porous structure, the substrate has an opening introduced into it which provides a fluid connection between the recess and the surroundings, and wherein the cross section of the opening is smaller than the object which remains within the recess once the second portion of the particles has been at least partly removed, so that the opening may be closed by means of the object so as to suppress the fluid connection to the surroundings.

19. The method as claimed in claim 11, wherein said provision of the substrate comprises providing a substrate comprising a circular recess and/or an elongated recess.

\* \* \* \* \*

UNITED STATES PATENT AND TRADEMARK OFFICE
CERTIFICATE OF CORRECTION

PATENT NO. : 11,268,122 B2
APPLICATION NO. : 15/679885
DATED : March 8, 2022
INVENTOR(S) : Thomas Lisec et al.

Page 1 of 1

It is certified that error appears in the above-identified patent and that said Letters Patent is hereby corrected as shown below:

In the Claims

Claim 11, Column 26, Line 3:
"...within the cavity may freely moves therein."
Should read as:
-- ...within the cavity freely moves therein. --

Signed and Sealed this
Ninth Day of August, 2022

Katherine Kelly Vidal
*Director of the United States Patent and Trademark Office*